(12) United States Patent
Shao et al.

(10) Patent No.: US 7,943,643 B2
(45) Date of Patent: May 17, 2011

(54) ARYL SUBSTITUTED PYRIDINES AND THE USE THEREOF

(75) Inventors: Bin Shao, Richboro, PA (US); R. Richard Goehring, Pipersville, PA (US); Samuel F. Victory, Newtown, PA (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 12/546,572

(22) Filed: Aug. 24, 2009

(65) Prior Publication Data
US 2010/0048626 A1 Feb. 25, 2010

Related U.S. Application Data

(62) Division of application No. 11/518,448, filed on Sep. 11, 2006, now Pat. No. 7,579,367, which is a division of application No. 10/235,673, filed on Sep. 6, 2002, now Pat. No. 7,105,549.

(60) Provisional application No. 60/317,526, filed on Sep. 7, 2001.

(51) Int. Cl.
*A61K 31/4418* (2006.01)
*C07D 213/26* (2006.01)

(52) U.S. Cl. ........................................ 514/355; 546/339
(58) Field of Classification Search .................. 514/355; 546/339
See application file for complete search history.

(56) References Cited

U.S. PATENT DOCUMENTS

| | | | |
|---|---|---|---|
| 3,149,109 A | 9/1964 | Rorig et al. | |
| 3,502,673 A | 3/1970 | Hepworth et al. | |
| 3,631,036 A | 12/1971 | Kim et al. | |
| 3,660,414 A | 5/1972 | Hardtmann et al. | |
| 3,709,888 A | 1/1973 | Hardtmann et al. | |
| 3,886,167 A | 5/1975 | Ash et al. | |
| 3,940,404 A | 2/1976 | Ash et al. | |
| 4,133,956 A | 1/1979 | Abdulla et al. | |
| 4,260,621 A | 4/1981 | Roch et al. | |
| 4,293,552 A | 10/1981 | Miesel | |
| 4,332,809 A | 6/1982 | Honma et al. | |
| 4,364,956 A | 12/1982 | Clark et al. | |
| 4,530,842 A | 7/1985 | Bormann | |
| 4,698,091 A | 10/1987 | Brunner et al. | |
| 4,701,208 A | 10/1987 | Los | |
| 4,762,835 A | 8/1988 | Whittle et al. | |
| 4,769,462 A | 9/1988 | Los | |
| 4,783,466 A | 11/1988 | Katoh et al. | |
| 4,912,218 A | 3/1990 | Coyle et al. | |
| 4,920,119 A | 4/1990 | Attwood et al. | |
| 4,962,109 A | 10/1990 | McDonald et al. | |
| 4,968,702 A | 11/1990 | Poletto et al. | |
| 5,010,200 A | 4/1991 | McDonald et al. | |
| 5,084,462 A | 1/1992 | Ackerman et al. | |
| 5,116,989 A | 5/1992 | Hale et al. | |
| 5,136,080 A | 8/1992 | Miller et al. | |
| 5,250,533 A | 10/1993 | Heinemann et al. | |
| 5,340,701 A | 8/1994 | Desobry | |
| 5,389,632 A | 2/1995 | Bru-Magniez et al. | |
| 5,403,934 A | 4/1995 | Batchelor et al. | |
| 5,405,553 A | 4/1995 | Terada et al. | |
| 5,418,233 A | 5/1995 | Linz et al. | |
| 5,563,268 A | 10/1996 | Linz et al. | |
| 5,587,380 A | 12/1996 | Miller et al. | |
| 5,591,746 A | 1/1997 | Miller et al. | |
| 5,597,827 A | 1/1997 | Miller et al. | |
| 5,597,828 A | 1/1997 | Miller et al. | |
| 5,602,156 A | 2/1997 | Kohn et al. | |
| 5,635,507 A | 6/1997 | Miller et al. | |
| 5,684,005 A | 11/1997 | Miller et al. | |
| 5,712,276 A | 1/1998 | Miller et al. | |
| 5,744,492 A | 4/1998 | Kohn et al. | |
| 5,756,524 A | 5/1998 | Riordan et al. | |
| 5,824,624 A | 10/1998 | Kleeman et al. | |
| 5,849,758 A | 12/1998 | Kleeman et al. | |
| 5,985,886 A | 11/1999 | Elliott et al. | |
| 6,008,161 A | 12/1999 | Kleemann et al. | |

(Continued)

FOREIGN PATENT DOCUMENTS

DE 30 12 597 A1 10/1980

(Continued)

OTHER PUBLICATIONS

Aggarwal, V., et al., "Reaction of α-Ketoketene S,N-Acetals with Cyanoacetamide: A New General Method for Substituted and Fused 4-(N-Alkylamino-, N-Arylamino-, or N-Morpholino)-3-cyano-2(1H)-pyridones," *Synthesis* 3:214-216, Georg Thieme Verlag, DE (1982).

Akopian, A.N., et al., "The tetrodotoxin-resistant sodium channel SNS has a specialized function in pain pathways," *Nat. Neurosci.* 2:541-548, Nature America Inc., USA (1999).

Al-Omran, F. and Al-Awadi, N., "Studies of Polyfunctionally Substituted Heteroaromatics: Synthesis of New Polyfunctionally Substituted Azabiaryls," *J. Chem. Res. Synop.* 10:392-393, The Royal Society of Chemistry, UK (1995).

(Continued)

*Primary Examiner* — Taofiq A Solola
(74) *Attorney, Agent, or Firm* — Sterne, Kessler, Goldstein & Fox P.L.L.C.

(57) ABSTRACT

This invention relates aryl substituted pyridines of Formula I:

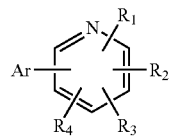

or a pharmaceutically acceptable salt, prodrug or solvate thereof, wherein Ar and $R_1$-$R_4$ are set in the specification. The invention is also directed to the use of compounds of Formula I for the treatment of neuronal damage following global and focal ischemia, for the treatment or prevention of neurodegenerative conditions such as amyotrophic lateral sclerosis (ALS), and for the treatment, prevention or amelioration of both acute or chronic pain, as antitinnitus agents, as anticonvulsants, and as antimanic depressants, as local anesthetics, as antiarrhythmics and for the treatment or prevention of diabetic neuropathy.

13 Claims, No Drawings

U.S. PATENT DOCUMENTS

| | | | |
|---|---|---|---|
| 6,057,346 | A | 5/2000 | Kohn et al. |
| 6,066,597 | A | 5/2000 | Kleemann et al. |
| 6,127,371 | A | 10/2000 | Elliott et al. |
| 6,335,354 | B2 | 1/2002 | Hogenkamp |
| 6,395,753 | B1 | 5/2002 | Kodama et al. |
| 6,414,011 | B1 | 7/2002 | Hogenkamp et al. |
| 6,552,188 | B2 | 4/2003 | Kodama et al. |
| 7,105,549 | B2 | 9/2006 | Shao et al. |
| 7,579,367 | B2 | 8/2009 | Shao et al. |
| 2001/0044428 | A1 | 11/2001 | Hogenkamp |
| 2002/0006947 | A1 | 1/2002 | Hogenkamp et al. |
| 2002/0040025 | A1 | 4/2002 | Hogenkamp et al. |
| 2003/0236273 | A1 | 12/2003 | Goehring et al. |
| 2004/0116388 | A1 | 6/2004 | Armistead et al. |
| 2004/0192691 | A1 | 9/2004 | Hogenkamp et al. |

FOREIGN PATENT DOCUMENTS

| | | | |
|---|---|---|---|
| DE | 32 39 573 | A1 | 5/1983 |
| DE | 32 45 950 | A1 | 7/1983 |
| EP | 0 096 657 | A2 | 12/1983 |
| EP | 0 123 700 | A1 | 11/1984 |
| EP | 0 200 024 | B1 | 11/1986 |
| EP | 0 271 195 | A1 | 6/1988 |
| EP | 0 362 578 | A1 | 4/1990 |
| EP | 0 389 236 | A2 | 9/1990 |
| EP | 0 389 236 | A3 | 2/1991 |
| EP | 0 428 268 | A2 | 5/1991 |
| EP | 0 446 604 | A2 | 9/1991 |
| EP | 0 446 604 | A3 | 2/1992 |
| EP | 0 480 258 | A2 | 4/1992 |
| EP | 0 480 258 | A3 | 9/1992 |
| EP | 0 507 962 | A1 | 10/1992 |
| EP | 0 518 798 | A2 | 12/1992 |
| EP | 0 550 900 | A1 | 7/1993 |
| EP | 0 518 798 | A3 | 12/1994 |
| EP | 0 706 795 | A2 | 4/1996 |
| EP | 1 052 238 | A1 | 11/2000 |
| FR | 1477021 | | 4/1967 |
| FR | 1536093 | | 9/1967 |
| GB | 2 095 240 | A | 9/1982 |
| HU | 190 839 | | 11/1986 |
| HU | 206 202 | B | 7/1987 |
| JP | 56-104883 | | 8/1981 |
| JP | 63-20234 | | 4/1988 |
| JP | 2-52360 | | 2/1990 |
| JP | 7-76542 | | 3/1995 |
| RU | 92004354 | A | 3/1995 |
| RU | 96101815 | A | 3/1998 |
| RU | 2171256 | C2 | 7/2001 |
| SU | 1790172 | A1 | 5/1995 |
| WO | WO 92/06085 | A1 | 4/1992 |
| WO | WO 93/10114 | A1 | 5/1993 |
| WO | WO 95/19358 | A1 | 7/1995 |
| WO | WO 96/40628 | A1 | 12/1996 |
| WO | WO 98/37068 | A1 | 8/1998 |
| WO | WO 98/47869 | A1 | 10/1998 |
| WO | WO 99/31062 | A1 | 6/1999 |
| WO | WO 99/31088 | A1 | 6/1999 |
| WO | WO 99/32468 | A1 | 7/1999 |
| WO | WO 99/38829 | A1 | 8/1999 |
| WO | WO 00/32192 | A1 | 6/2000 |
| WO | WO 00/39087 | A2 | 7/2000 |
| WO | WO 00/57877 | A1 | 10/2000 |
| WO | WO 00/39087 | A3 | 11/2000 |
| WO | WO 01/47904 | A1 | 7/2001 |
| WO | WO 01/53288 | A1 | 7/2001 |
| WO | WO 01/68612 | A2 | 9/2001 |
| WO | WO 01/68612 | A3 | 3/2002 |
| WO | WO 02/24679 | A1 | 3/2002 |

OTHER PUBLICATIONS

Amine, M.S., "Utilities of 4-(4'-Benzyl Phenyl)-6-Arylpyrimidine-2-Thiones for the Synthesis of Biologically Active Condensed and Non-Condensed Heterocycles," *Egypt. J. Chem.* 41:267-276, The National Information and Documentation Centre, EG (1998).

Backonja, M., et al., "Gabapentin for the Symptomatic Treatment of Painful Neuropathy in Patients With Diabetes Mellitus," *J. Am. Med. Assoc.* 280:1831-1836, American Medical Association, USA (1998).

Baker, M.D. and Wood, J.N., "Involvement of Na+ channels in pain pathways," *Trends Pharm, Sci.* 22:27-31, Elsevier Science Ltd., UK (Jan. 2001).

Baldwin, J.E., et al., "Concise Syntheses of Acromelic Acid A and Allo-Acromelic Acid A," *Tetrahedron Lett.* 39:707-710, Pergamon, UK (1998).

Bennett, G.J., "Neuropathic Pain: New Insights, New Interventions," *Hosp. Prac.* 33:95-98, 101-104, 107-110, 113-114, The McGraw-Hill Companies, USA (1998).

Bensimon, G., et al., "A Controlled Trial of Riluzole in Amyotrophic Lateral Sclerosis," *New Eng. J. Med.* 330:585-591, The Massachusetts Medical Society, USA (1994).

Benson, S.C., et al., "Indole as a Dienophile in Inverse Electron Demand Diels-Alder Reactions: Reactions with 1,2,4-Triazines and 1,2-Diazines,"*J. Org. Chem.* 55:3257-3269, The American Chemical Society, USA (1990).

Berg, K.E., et al., "Covalently Linked Ruthenium(II)-Manganese(II) Complexes: Distance Dependence of Quenching and Electron Transfer," *Eur. J. Inorg. Chem.* 4:1019-1029, Wiley-VCH Verlag GmbH, DE (Apr. 2001).

Bettman, B., et al., "Dissociation Constants of Organic Boric Acids," *J. Am. Chem. Soc.* 56:1865-1870, Mack Printing Company, USA, (1934).

Bowsher, D., "Neurogenic pain syndromes and their management," *Br. Med. Bull.* 47:644-666, Oxford University Press, UK (1991).

Brown, C.M., et al., "Neuroprotective properties of lifarizine compared with those of other agents in a mouse model of focal cerebral ischaemia," *Br. J. Pharmacol.* 115:1425-1432, Stockton Press, UK (1995).

Buchan, A.M., et al., "AMPA Antagonists: Do They Hold More Promise for Clinical Stroke Trials Than NMDA Antagonists?" Suppl. *Stroke 24*:I-148-I-152, American Heart Association, USA (1993).

Burdeska, K., et al., "Über die Herstellung von Styryl- und Stilbenyl-Derivaten des Pyrimidins," *Helv. Chim. Acta.* 64:113-152, Schweizerische Chemische Gesellschaft, CH (1981).

Cabrerizo, M.A. and Soto, J.L., "Sintesis De Heterociclos. III. 2-Amino-3,5-diciano-4-aril-6-alcoxipiridinas a partir de bencilidenmalononitrilos," *An. Quim.* 70:951-958, La Real Sociedad Española de Fisica y Química, ES (1974).

Carver, A.C. and Foley, K.M., "Palliative Care," in: *Cancer Medicine*, Holland, J.F., et al., eds., Williams & Wilkins, Baltimore, MD, pp. 992-1000, USA (1997).

Catterall, W.A., "Common modes of drug action on Na+ channels: local anesthetics, antiarrhythmics and anticonvulsants," *Trends Pharmacol. Sci.* 8:57-65, Elsevier Publications Cambridge, UK (1987).

Catterall, W.A., "Neurotoxins That Act on Voltage-Sensitive Sodium Channels in Excitable Membranes," *Ann. Rev. Pharmacol. Toxicol* 20:15-43, Annual Reviews Inc., USA (1980).

Catterall, W.A., "Structure and Function of Voltage-Sensitive Ion Channels," *Science* 242:50-61, American Association for the Advancement of Science, USA (1988).

Cavallini, G., et al., "Antiviral Compounds. X. Aromatic mono-and dialdehydes," *Chem. Abstracts 62*:Abstract No. 5217h, The American Chemical Society, USA (1965).

Cavallini, G., et al., "Chemioterapici Antivirali, Nota X—Mono e bis aldeidi aromatiche," *Il Farmaco Ed. Sc.* 19:964-971, Il Farmaco, IT (1964).

Chacón, M. del C., et al., "Synthèse d'hétérocycles. XX (1). Réaction du malononitrile avec quelques cinnamonitriles," *J. Heterocycl. Chem.* 19:421-423, Wiley-Blackwell, USA (1982).

Chadda, V.S. and Mathur, M.S., "Double Blind Study of the Effects of Diphenylhydantoin Sodium on Diabetic Neuropathy," *Jr. Asso. Phys. Ind.* 26:403-406, Association of Physicians of India, IN (1978).

Chambers, R.J., et al., "Biarylcarboxamide Inhibitors of Phosphodiesterase IV and Tumor Necrosis Factor-α," *Bioorg. Med. Chem. Lett.* 7:739-744, Pergamon Press, UK (1997).

Chen, C., et al., "A Convenient Synthetic Method for Trisubstituted s-Triazines," *J. Org. Chem.* 60:8428-8430, The American Chemical Society, USA, (1995).

Clark, M. and Post, R.M., "Carbamazepine, but not caffeine, is highly selective for adenosine $A_1$ binding sites," *Eur. J. Pharmacol.* 164:399-401, Elsevier Science Publishers B.V., UK(1989).

Collins, S.L., et al., "Antidepressants and Anticonvulsants for Diabetic Neuropathy and Postherpetic Neuralgia: A Quantitative Systematic Review," *J. Pain Symptom Management* 20:449-458, Elsevier, UK (Dec. 2000).

Coward, K., et al., "Plasticity of Ttx-sensitive sodium channels PN1 and Brain Iii in injured human nerves," Neuroreport 12:495-500, Lippincott Williams & Wilkins, Usa (Mar. 2001).

Creveling, C.R., et al., "Batrachotoxin-Induced Depolarization and [$^3$H]Batrachotoxinin-A 20α-Benzoate Binding in a Vesicular Preparation from Guinea Pig Cerebral Cortex. Inhibition by Local Anesthetics," *Mol. Pharmacol.* 23:350-358, The American Society for Pharmacology and Experimental Therapeutics, USA (1983).

D'Agostino, V.F., et al., "Absorption Spectra of Tetracyclones. V," *J. Org. Chem.* 23:1539-1544, The American Chemical Society, USA (1958).

Daines R.A., et al., "Quinine Analogs as Non-Peptide Calcitonin Gene-Related Peptide (CGRP) Receptor Antagonists," *Bioorg. Med. Chem. Lett.* 7:2673-2676, Pergamon Press, UK (1997).

Daves, G.D., et al., "Pyrimidines. XIII. 2- and 6-Substituted 4-Pyrimidinecarboxylic Acids (1a)," *J. Heterocyclic Chem.* 1:130-133, Wiley-Blackwell, USA (1964).

Denicoff, K.D., et al., "Efficacy of Carbamazepine Compared With Other Agents: A Clinical Practice Survey," *J. Clin. Psychiatry* 55:70-76, Physicians' Postgraduate Press, Inc., USA (1994).

DeWald, H.A., et al., "Pyrazolodiazepines. 3. 4-Aryl-1,6,7,8-tetrahydro-1,3-dialkylpyrazolo[3,4-e][1,4]diazepines as Antidepressant Agents," *J. Med. Chem.* 24:982-987, The American Chemical Society, USA (1981).

Domagala, J.M. and Peterson, P., "New 7-Substituted Quinolone Antibacterial Agents. II. The Synthesis of 1-Ethyl-1,4-dihydro-4-oxo-7-(pyrazolyl, isoxazolyl, and pyrimidinyl)-1,8-naphthyridine and quinolone-3-carboxylic Acids," *J. Heterocyclic Chem.* 26:1147-1158, Wiley-Blackwell, USA (1989).

Donaldson, I., "Tegretol: A double blind trial in tinnitus," *J. Laryngol. Otol.* 95:947-951, Headley Brothers Ltd., UK (1981).

Dreixler, J.C., et al., "Block of rat brain recombinant Sk channels by tricyclic antidepressants and related compounds," *Eur. J. Pharmacol.* 401:1-7, Elsevier Science B.V., UK (Jul. 2000).

El-Kafrawy, A.F., et al., "A Facile One-step Conversion of β-Benzoylacrylic Acids into Some Interesting Heterocycles and Study of their Microbiological Activity," *J. Chem. Soc. Pak.* 14:59-66, Chemical Society of Pakistan, PK (1992).

England, J.D., et al., "Sodium channel accumulation in humans with painful neuromas," *Neurology* 47:272-276, Lippincott-Raven, USA (1996).

English language translation of Georgian Patent Office Search Report for Patent Application No. AP 2001 004969, dated Apr. 1, 2004.

Fischer, G.W., "Tetrazole Compounds. 8[1]. Synthesis of Tetrazolylpyrimidines from Tetrazolyl-substituted Enamino Ketones," *J. Heterocyclic Chem.* 30:1517-1519, Wiley-Blackwell, USA (1993).

Foley, K.M., "Supportive Care and Quality of Life, Management of Cancer Pain," in: *Cancer: Principles & Practice of Oncology*, Fifth Edition, DeVita Jr., V.T., et al., eds. Lippincott-Raven Publishers, Philadelphia, PA, pp. 2807-2841 (1997).

Foley, K.M., "Supportive Care and Quality of Life, Management of Cancer Pain," in: *Cancer: Principles & Practice of Oncology*, Sixth Edition, DeVita Jr., V.T., et al., eds. Lippincott-Williams & Wilkins Publishers, Philadelphia, PA pp. 2977-3011 (Jan. 2001).

Fuentes, L., et al., "Amalgam (Na.Hg) Reduction of some 4-Substituted-2-amino-3,5-dicyano-6-methoxypyridines. New Evidence Regarding the Oxidation Step in their Synthesis," *J. Heterocycl. Chem.* 36:481-483, Wiley-Blackwell, USA (Mar./Apr. 1999).

Fuentes, L., et al., "Sintesis de Heterociclos. XVI Reaccion del Malonitrilo con Bencilidenmalonitrilos en Presencia de Aminas," *An. Quim. Ser. C* 76:68-69, Real Sociedad Española de Fisica y Quimica, ES (1980).

Gainer, H., "Synthesis of Pyrazinoic Acid," *J. Org. Chem.* 24:691, The American Chemical Society, USA (1959).

Giroux, A., et al., "One Pot Biaryl Synthesis via in situ Boronate Formation," *Tetrahedron Lett.* 38:3841-3844, Pergamon Press, UK (1997).

Gomez-Parra, V., et al., "New Cardiotonic Agents Related to Amrinone: Synthesis of 1,2-Dihydro-5-arylpyridin-2-ones," *Arch. Pharm.* 325:483-490, VCH Verlagsgesellschaft mbH, DE (1992).

Görlitzer, K. and Diers, K., "Pyridine and Pyrimidine aus Etacrynsäure," *Pharmazie* 52:97-100, Eschborn Govi-Verlag Pharmazeutischer Verlag GmbH, DE (1997).

Görlitzer, K. and Düwel, W., "Pyridin-Verbindungen aus Etacrynsäure, 2. Mitteilung," *Arch. Pharm. (Weinheim)* 325:357-359, VCH Verlagsgesellschaft mbH, DE (1992).

Graham, S.H., et al., "A Dose-Response Study of Neuroprotection Using the AMPA Antagonist NBQX in Rat Focal Cerebral Ischemia," *J. Pharmacol. Exp. Ther.* 276:1-4, Williams and Wilkins, USA (1996).

Graham, S.H., et al., "Neuroprotective Effects of a Use-Dependent Blocker of Voltage-Dependent Sodium Channels, BW619C89, in Rat Middle Cerebral Artery Occlusion," *J. Pharmacol. Exp. Ther.* 269:854-859, Williams and Wilkins, USA (1994).

Grunze, H., et al., "Modulation of Calcium and Potassium Currents by Lamotrigine," *Neuropsychobiology* 38:131-138, S. Karger AG, DE (1998).

Hamill, O.P., et al., "Improved Patch-Clamp Techniques for High-Resolution Current Recording from Cells and Cell-Free Membrane Patches," *Pflügers Arch.* 391:85-100, Springer-Verlag, DE (1981).

Honma, Y., et al., "Antiallergic Agents. 2. N-(1H-Tetrazol-5-yl)-6-phenyl-2- pyridinecarboxamides," *J. Med. Chem.* 26:1499-1504, The American Chemical Society, USA (1983).

Hungarian Patent Office Novelty Search Report for Hungarian Patent Application No. P 05 00138, dated Mar. 9, 2005.

Hungarian Patent Office Novelty Search Report for Hungarian Patent Application No. P 05 00131, dated Mar. 9, 2005.

Hungarian Patent Office, Novelty Search Report for Application No. P 03 00466, dated Aug. 7, 2003.

Hunskaar, S., et al., "Formalin test in mice, a useful technique for evaluating mild analgesics," *J. Neurosci. Methods* 14:69-76, Elsevier Science Publishers B.V., UK (1985).

Hussain, S.M., et al., "New Synthesis of Polyfunctionally Substituted 2-Mercaptopyridines and Fused Pyridines," *Gazz. Chim. Ital.* 124:97-101, Società Chimica Italiana, IT (1994).

Iwamoto, K., et al., "Ring Transformation of Fused Pyridazines. III. 1-Substituted Phthalazines with Ynamines," *Chem. Pharm. Bull.* 43:679-682, Pharmaceutical Society of Japan, JP (1995).

Iwasaki, Y., et al., "CNQX prevents spinal motor neuron death following sciatic nerve transection in newborn rats," *J. Neuro. Sci.* 134:21-25, Elsevier Science B.V., UK (1995).

Kagabu, S. and Mizoguchi, S., "A Unique Synthetic Method for Pyridine-Ring Containing Ter-, Quater- and Quinquearyl and Vinylogues by Thermolysis of 2,2-Dichlorocyclopropylmethyleneamines," *Synthesis* 3:372-376, Thieme, USA (1996).

Kajander, K.C. and Bennet, G.J., "Onset of a Painful Peripheral Neuropathy in Rat: A Partial and Differential Deafferentation and Spontaneous Discharge in Aβ and Aδ Primary Afferent Neurons," *J. Neurophysiol.* 68:734-744, American Physiological Society, USA (1992).

Karamysheva, L.A., et al., "New Heterocyclic Liquid Crystalline Compounds," *Mol. Cryst. Liq. Cryst.* 67:241-251, Gordon and Breach Science Publishers, Inc., NL (1981).

Katagiri, N., et al., "Cycloadditions in Syntheses. XXXVII. Syntheses of 6-Trifluoromethyl-1,2,4-triazines and -1,2,4-triazin-5-ones and Their Pericyclic Reactions with Olefins," *Chem. Pharm. Bull.* 36:3354-3372, Pharmaceutical Society of Japan, JP (1988).

Kauffmann, T. and Wolf, D., "Synthese von Amidrazonen aus Nitrilen und Natriumhydrazid," *Angew. Chem.* 75:344, Verlag Chemie GmbH, DE (1963).

Keating, M.T. and Sanguinetti, M.C., "Molecular Genetic Insights into Cardiovascular Disease," *Science* 272:681-685, American Association for the Advancement of Science, USA (1996).

Kim, S.H. and Chung, J.M., "An experimental model for peripheral neuropathy produced by segmental spinal nerve ligation in the rat," *Pain* 50:355-363, Elsevier Science Publishers B.V., UK (1992).

King, *Med Chem: Principle and Practice*, The Royal Society of Chemistry, Thomas Graham House, UK, pp. 206-208 (1994).

Kingery, W.S., "A critical review of controlled clinical trials for peripheral neuropathic pain and complex regional pain syndromes," *Pain* 73:123-139, Elsevier Science B.V., UK (1997).

Kirsch, G.E., "Na+ Channels: Structure, Function, and Classification," *Drug Develop. Res.* 33:263-276, Wiley-Liss, Inc., USA (1994).

Klauschenz, E., et al., "Potentielle Kardiotonika. 2. Mitteilung: Synthese und pharmakologische Eigenschaften von 5-(pyrid-4-yl)- und 5-phenylsubstituierten 3-Cyan-6-methyl-2-oxaalkylamino-pyridinen" *Pharmazie* 44:23-25, VEB Verlag Volk und Gesundheit, DE (1989).

Konakahara, T., et al., "One-pot synthesis of 2-(trifluoromethyl)pyridines from N-silyl-1-aza-allyl anions with trifluoroacetylketene diethyl ketal or (E)-1,1,1- trifluoro-4-phenylbut-3-en-2-one," *J. Chem. Soc., Perkin Trans.* 1:2803-2806, The Royal Society of Chemistry, UK (1999).

Konno, S., et al., "Studies on as-Triazine Derivatives. VI. Introduction of Aryl Groups to the 5-Position of 1,2,4-Triazines," *Heterocycles* 23:2807-2810, Elsevier Science, UK 1985.

Kumar, A., et al., "Keten Dithioacetals. Part 11. Reaction of 3-Cyano-4-methylthio-2(1H)-pyridones with Hydrazine and Guanidine: Synthesis of Novel Substituted and Fused Pyrazolo[4,3-c]pyridone and Pyrido[4,3-d]pyrimidine derivatives," *J. Chem. Soc.*, Perkins Trans. 1:857-862, The Royal Society of Chemistry, UK (1978).

Kuo, C.-C. and Bean, B.P., "Slow Binding of Phenytoin to Inactivated Sodium Channels in Rat Hippocampal Neurons," *Mol. Pharmacol.* 46:716-725, Williams and Wilkins, USA (1994).

Kuo, C.-C., et al., "Carbamazepine Inhibition of Neuronal Na+ Currents: Quantitative Distinction from Phenytoin and Possible Therapeutic Implications," *Mol. Pharmacol.* 51:1077-1083, American Society for Pharmacology and Experimental Therapeutics, USA (1997).

Lampe, H. and Bigalke, H., "Carbamazepine blocks NMDA-activated currents in cultured spinal cord neurons," *NeuroReport* 1:26-28, Rapid Communications of Oxford Ltd., UK (1990).

Latif, N., et al., "Malononitriles & Cyanoesters: Part VI-Synthesis of New Biologically Active Cyanopyridines,"*Indian J. Chem.* 20B:147-149, Publications and Information Directorate, IN (1981).

Leff, P. and Dougall, I.G., "Further concerns over Cheng-Prusoff analysis," *TiPS* 14:110-112, Elsevier Science Publishers Ltd., UK (1993).

Li, J.J., et al., "1,2-Diarylcyclopentenes as Selective Cyclooxygenase-2 Inhibitors and Orally Active Anti-inflammatory Agents," *J. Med. Chem.* 38:4570-4578, The American Chemical Society, USA (1995).

Liao, T.K., et al., "Synthetic Studies of the Antitumor Antibiotic Streptonigrin. II. Synthesis of the C-D Ring Portion of Streptonigrin," *J. Heterocycl. Chem.* 13:1283-1288, Wiley-Blackwell, USA (1976).

MacFarlane, B.V., et al., "Chronic Neuropathic Pain and Its Control by Drugs," *Pharmacol. Ther.* 75:1-19, Elsevier Science Inc., UK (1997).

Mackin, G.A., "Medical and Pharmacologic Management of Upper Extremity Neuropathic Pain Syndromes," *J. Hand Ther.* 10:96-109, Hanley & Belfus, Inc., USA (1997).

Majumdar, B., et al., "An electrocochleographic study of the effects of lignocaine on patients with tinnitus," *Clin. Otolaryngol* 8:175-180, Blackwell Scientific Publications, USA (1983).

Mano, M., et al., "Anticoccidials. V. Synthesis and Anticoccidial Activity of 2(1H)-Pyrazinone 4-Oxide Derivatives," *Chem. Pharm. Bull.* 28:2734-2747, Pharmaceutical Society of Japan, JP (1980).

Marcoux, J.-F., et al., "A General Copper-Catalyzed Synthesis of Diaryl Ethers," *J. Am. Chem. Soc.* 119:10539-10540, The American Chemical Society, USA (1997).

Massarani, E. and Mauri, L., "Antiviral Compounds. VIII. New glyoxal derivatives of diphenyl ether," *Chem. Abstracts* 62:Abstract No. 5217e, The American Chemical Society, USA (1965).

Massarani, E. and Mauri, L., "Chemioterapici Antivirali, Nota VIII—Nuovi gliossali derivati del difeniletere," *Il Farmaco Ed. Sci.* 19:958-963, Il Farmaco, IT (1964).

Matsumoto, I., "N-Tetrazol-5-yl-6-phenyl-2-pyridinecarboxamides," *Chem. Abstr.* 96:181290v, The American Chemical Society, USA (1982).

McQuay, H.J., et al., "A systematic review of antidepressants in neuropathic pain," *Pain* 68:217-227, Elsevier Science B.V., UK (1996).

Meadows, H.J., et al., "The neuroprotective agent sipatrigine (BW619C89) potently inhibits the human tandem pore-domain $K^+$ channels TREK-1 and TRAAK," *Brain Res.* 892:94-101, Elsevier Science B.V., UK (Feb. 2001).

Møller, A.R., "Similarities Between Chronic Pain and Tinnitus," *Am. J. Otol.* 18:577-585, Lippincott-Raven Publishers, USA (1997).

Moshé, S.L., "Mechanisms of action of anticonvulsant agents," *Neurology 55 (Suppl. 1)*:S32-S40, Lippincott Williams & Wilkins, USA (Sep. 2000).

Murata, M., et al., "Palladium-Catalyzed Borylation of Aryl Halides or Triflates with Dialkoxyborane: A Novel and Facile Synthetic Route to Arylboronates," *J. Org. Chem.* 65:164-168, The American Chemical Society, USA (Dec. 1999/ Jan. 2000).

Neuromuscular Disease Center, "Ion Channels, Transmitters, Receptors, and Disease: Sodium Channels," available online at http://www.neuro.wustl.edu/neuromuscular/mother/chan.html, pp. 5-10 (2005).

Nezu, Y., et al., "Dimethoxypyrimidines as Novel Herbicides. Part 1. Synthesis and Herbicidal Activity of Dimethoxyphenoxyphenoxypyrimidines and Analogues," *Pestic. Sci.* 47:103-113, John Wiley and Sons Ltd., UK (1996).

Ohizumi, Y., et al., "Specific Inhibition of [3EH] Saxitoxin Binding to Skeletal Muscle Sodium Channels by Geographutoxin II, a Polypeptide Channel Blocker," *J. Biol. Chem.* 261:6149-6152, The American Society of Biological Chemists, Inc., USA (1986).

Ohta, A., et al., "Reactions of the Monoxides of 2,6-Distributed Pyrazines with Phosphoryl Chloride and Acetic Anhydride," *J. Heterocyclic Chem.* 20:311-320, Wiley-Blackwell, USA (1983).

Pallas, M., et al., "Chemical synthesis of new pyridine derivatives acting as inhibitors of phosphodiesterase," *Pharm. Pharmacol. Lett.* 3:36-39, Springer-Verlag, DE (1993).

Partial English language Translation for Japanese Unexamined Patent Application No. JP 56-104883, published 1981.

Pavlyuchenko, A.I., et al., "Synthesis and Structure of Mesomorphic 2-cyano-5-[p-alkyl(alkoxy)phenyl]-pyridines," *Chem. Heterocycl. Compounds* 16:681-684, Plenum Publishing Corporation, DE (1981).

Petrovskii, A.S, et al., "Phosphazoreaction in the Series of 2-Amino-3,5-dicyano-4-aryl-6-methoxypyridines," *Zh. Obshch. Khim.* 53:1187-1188, Nauka, RU (1983).

Petrovskii, A.S., et al., "Phosphazo reaction in a series of 2-amino-3,5-dicyano4-aryl-6-methoxypyridines," CAPLUS Accession No. 1983:505364, Chemical Abstracts Service (1983).

Piettre, S.R., et al., "Monoaryl- and Bisaryldihydroxytropolones as Potent Inhibitors of Inositol Monophosphatase," *J. Med. Chem.* 40:4208-4221, The American Chemical Society, USA (1997).

Quintela, J.M. and Peinador, C., "A Ready One-pot Preparation for 7-Oxa(or thia)-3,4,6-triazabenz[d,e]anthracene and 7-Oxa-3,4,6,9-tetrabenz[d,e]anthracene Derivatives," *Tetrahedron* 52:10497-10506, Pergamon Press, UK (1996).

Ragsdale, D.S., et al., "Frequency and Voltage-Dependent Inhibition of Type IIA Na+ Channels, Expressed in a Mammalian Cell Line, by Local Anesthetic, Antiarrhythmic, and Anticonvulsant Drugs," *Mol. Pharmacol.* 40:756-765, Williams & Wilkins, USA (1991).

Rätz, R. and Schroeder, H., "Products from Reaction of Hydrazine and Thionooxamic Acid and Their Conversion into Heterocyclic Compunds," *J. Org. Chem.* 23:1931-1934, The American Chemical Society, USA (1958).

Reddy, A.C.S., et al. "A Novel Method for the Synthesis of Isoxazolo and Pyrazolo Pyridines Using Hypervalent Iodine Reagent," *Synth. Commun.* 27:2217-2222, Marcel Dekker, Inc., USA (1997).

Reddy, A.C.S., et al., "Fluoro-organics: trifluoromethyl group-induced O-alkylation of pyridin-2-ones," *J. Fluorine Chem.* 78:21-25, Elsevier Science S.A., UK (1996).

Roden, D.M., "Mechanisms and Management of Proarrhythmia," *Am. J. Cardiol. 82*:491-571, Excerpta Medica, Inc., USA (1998).

Rogawski, M.A. and Porter, R.J., "Antiepileptic Drugs: Pharmacological Mechanisms and Clinical Efficacy with Consideration of Promising Developmental Stage Compounds," *Pharmacol. Rev. 42*:223-286, American Society for Pharmacology and Experimental Therapeutics, USA (1990).

Rottländer, M. and Knochel, P., "Multiple Cross-Coupling Reactions of Aryl and Benzylic Zinc Halides with Aryl Halides and Triflates in Solid-Phase Synthesis of Polyfunctional Aromatics," *Synlett 9*:1084-1086, Thieme, USA (1997).

Rykowski, A. and Makosza, M., "Reaction of 1,2,4-Triazines with Nitronate Anions, Direct Nucleophilic Acylation of 1,2,4-Triazines," *Tetrahedron Lett. 25*:4795-4796, Pergamon Press Ltd., UK (1984).

Rykowski, A., et al., "Reactions of 1,2,4-Triazines with Nitromethide Ion. A Convenient Method of Preparation of 1,2,4-Triazin-5-ylcarbaldehyde Oximes and their Synthetic Applications," *J. Heterocycl. Chem. 33*:1567-1571, Wiley-Blackwell, USA (1996).

Said, G., "Diabetic neuropathy: an update," *J. Neurol. 243*:431-440, Springer-Verlag, DE (1996).

Sakamoto, T., et al., "Studies on Pyrimidine Derivatives. XVI. Site Selectivity in the Homolytic Substitution of Simple Pyrimidines," *Chem. Pharm. Bull. 28*:571-577, Pharmaceutical Society of Japan, JP (1980).

Salman, A.S.S., "Synthesis and reaction of cyanopyridone derivatives and their potential biological activities," *Pharmazie 54*:178-183, Eschborn Govi-Verlag Pharmazeutischer Verlag GmbH, DE (1999).

Sammour, A., et al., "Some Reactions of the 2 (1H)-Pyridones Prepared from 4,4-Dimethoxychalcone and Anisal Acetone," *U.A.R.J. Chem. 14*:581-598, The National Information and Documentation Centre (1971).

Sato, N., et al., "Studies on pyrazines. Part 34. Synthetic approach, stability and tautomerism of 2,6-dihydroxypyrazines," *J. Chem. Soc., Perkin Trans. 1*:3167-3172, The Royal Society of Chemistry, UK (1997).

Satyanarayana, J., "Cyclocondensation of α-Oxoketene N,S-Acetals with β-Lithioamino-β-Substituted Acrylonitriles: A Facile Route to 2,6-Substituted 4-Amino-3-cyanopyridines," *Synthesis 10*:889-890, Georg Thieme Verlag, DE (1991).

Saudek, C.D., et al., "Phenytoin in the treatment of diabetic symmetrical polyneuropathy," *Clin. Pharmacol. Ther. 22*:196-199, Mosby Year Book, USA (1997).

Scadding, J.W., "Neuropathic Pain," in: *Diseases of the Nervous System: Clinical Neurobiology*, Asbury, A.K., et al., eds., W.B. Saunders, Philadelphia, PA, pp. 858-872 (1992).

Scadding, J.W., "Peripheral neuropathies," in: *Textbook of Pain*, 2nd Edition, Wall, P.D. and Melzack, R., eds., Churchill Livingstone, Edinburgh, Scotland, pp. 522-534 (1992).

Schirrmacher, K., et al., "Effects of carbamazepine on membrane properties of rat sensory spinal ganglion cells in vitro," *Eur. Neuropsychopharmacol. 5*:501-507, Elsevier Science B.V., UK (1995).

Seada, M., et al., "Reactions with 2-amino-3,5-dicyanopyridines," Database CAPLUS Accession No. 114:81740, Chemical Abstracts Service (1991).

Seada, M., et al., "Reactions with 2-Amino-3,5-Dicyanopyridines," *Orient. J. Chem. 5*:273-280, Oriental Scientific Publishing Co., IN (1989).

Seada, M., et al., "Synthesis and Biological Activities of Some New Pyridazine Derivatives," *J. Chin. Chem. Soc. 36*:241-249, Chinese Chemical Society, CN, (1989).

Senga, K., et al., "New Syntheses of Pyrido[3,2-*d*]pyrimidines," *J. Heterocycl. Chem. 19*:805-808, Wiley-Blackwell, USA (1982).

Sheardown, M.J., et al., "AMPA, but not NMDA, receptor antagonism is neuroprotective in gerbil global ischaemia, even when delayed 24 h," *Eur. J. Pharmacol. 236*:347-353, Elsevier Science Publishers B.V., UK (1993).

Shkurko, O.P., et al., "Electronic Spectra of asym-Triazinyl Groups," *Chem. Heterocycl. Compd. 23*:216-221, Plenum Publishing Corporation, DE (1987).

Simpson, J.J. and Davies, W.E., "Recent advances in the pharmacological treatment of tinnitus," *Trends Pharmacol. Sci. 20*:12-18, Elsevier Science London, UK (Jan. 1999).

Sindrup, S.H. and Jensen, T.S., "Pharmacologic treatment of pain in polyneuropathy," *Neurol. 55*:915-920, Lippincott, Williams & Wilkins, USA (Oct. 2000).

Singh, G., et al., "Synthesis of nucleosides of pyrido-[2,3-*d*]pyrimidines and their microbial activity," *Indian J. Chem. 37B*:517-520, National Institute of Science Communication, IN (1998).

Stefani, A., et al., "Lamotrigine inhibits $Ca^{2+}$ currents in cortical neurons: functional implications," *Eur. J. Pharmacol. 307*:113-116, Elsevier Science B.V., UK (1996).

Stys, P.K., et al., "Ionic Mechanisms of Anoxic Injury in Mammalian CNS White Matter: Role of $Na^+$ Channels and $Na^+$-$Ca^{2+}$ Exchanger," *J. Neurosci. 12*:430-439, Society for Neuroscience, USA (1992).

Tanaka, A., et al., "Inhibitors of Acyl-CoA:Cholesterol O-Acyltransferase. 3. Discovery of a Novel Series of N-Alkyl-N-[(fluorophenoxy)benzyl]-N'-arylureas with Weak Toxicological Effects on Adrenal Glands," *J. Med. Chem. 41*:4408-4420, The American Chemical Society, USA (1998).

Taylor, C.P. and Meldrum, B.S., "$Na^+$ channels as targets for neuroprotective drugs," *Trends Pharmacol. Sci. 16*:309-316, Elsevier Science Ltd., UK, (1995).

Taylor, C.P., "Mechanisms of action of gabapentin," *Rev. Neurol.* (Paris) 153:1S39-1S45, Masson, FR (1997).

Taylor, C.P., et al., "A summary of mechanistic hypotheses of gabapentin pharmacology," *Epilepsy Res. 29*:233-249, Elsevier Science B.V., UK (1998).

Tonndorf, J., "The analogy between tinnitus and pain: A suggestion for a physiological basis of chronic tinnitus," *Hear Res. 28*:271-275, Elsevier Science Publishers B.V., UK (1987).

Trojanowski, J.Q., "Alzheimer's Disease, Parkinson's Disease, and Related Brain Disorders: Brief Overview for Patients and Caregivers," available online at http://www.uphs.upenn.edu/cndr/Research/pages/ADPD.html, The Trustees of the University of Pennsylvania, USA (1999).

Troschütz, R., et al., "Easy synthesis of 6-aryl-2-methylnicotinic acid derivatives," Database CAPLUS Accession No. 114:101664, Chemical Abstracts Service (1991).

Troschütz, V.R. and Nietsch, K.-H., "Einfache Synthese von 6-Aryl-2-methylnicotinsäure-Derivaten," *Chem. Ztg. 114*:321-322, Huethig Publishing Ltd., DE (1990).

Veldman, P.H.J.M., et al., "Signs and symptoms of reflex sympathetic dystrophy: prospective study of 829 patients," *The Lancet 342*:1012-1016, The Lancet Publishing Group, UK (1993).

Verndoorn, T.A., et al., "Functional Properties of Recombinant Rat $GABA_A$ Receptors Depend upon Subunit Composition," *Neuron 4*:919-928, Cell Press, USA (1990).

Wasfy, A.A.F., et al., "Novel Pyrimidine Congeners as Antimicrobial Agents," *Sulfur Lett. 19*:45-53, Harwood Academic Publishers GmbH, DE (1995).

Wasfy, A.A.F., et al., "Synthesis and Reactions of 6(4)-(P-Benzylphenyl)-4(6)-Phenylpyrimidine-2(1H) Thione," *Heterocycl. Commun. 2*:375-381, Freund Publishing House Ltd., IL (1996).

Woodward, R.M., et al., "Effects of Steroids on γ-Aminobutyric Acid Receptors Expressed in *Xenopus* Oocytes by Poly(A)$^+$ RNA from Mammalian Brain and Retina," *Mol. Pharmacol. 41*:89-103, Williams and Wilkins, USA (1992).

Wrathall, J.R., et al., "Amelioration of Functional Deficits from Spinal Cord Trauma with Systemically Administered NBQX, an Antagonist of Non-N-methyl-D-aspartate receptors," *Exp. Neurol. 137*:119-126, Academic Press, Inc., USA (1996).

Abstract of Hungarian Patent Application No. P 03 00466, filed Mar. 12, 2001.

Abstract of Hungarian Patent Application No. P 03 03124, filed Sep. 10, 2001.

Chemical Abstracts English language abstract of EP 480 258 A2 (Document FP22), Database CAPLUS Accession No. 1992:426351, Chemical Abstracts Service (1992).

Chemical Abstracts English language abstract of FR 1,477,021 (Document FP1), Database CAPLUS Accession No. 1967:521357, Chemical Abstracts Service (1967).

Chemical Abstracts English language abstract of FR 1,536,093 (Document FP2), Database CAPLUS Accession No. 1969:481429, Chemical Abstracts Service (1969).

Chemical Abstracts English language abstract of JP 2-52360 (Document FP15), Database CAPLUS Accession No. 1990:523850, Chemical Abstracts Service (1990).

Dialog File 351, Accession No. 10250554, Derwent WPI English language abstract for JP 7-76542, published 1995 (Document FP30).

Dialog File 351, Accession No. 12589045, Derwent WPI English language abstract for WO 99/31062 A1, published 1999 (Document FP39).

Dialog File 351, Accession No. 13240262, Derwent WPI English language abstract for WO 00/32192 A1, published 2000 (Document FP43).

Dialog File 351, Accession No. 14030103, Derwent WPI English language abstract for WIPO Patent Publication No. WO 01/47904 A1, Derwent Information Ltd. (Jul. 2001) (Document FP48).

Dialog File 351, Accession No. 14038004, Derwent WPI English language abstract for WIPO Patent Publication No. WO 01/53288 A1, Derwent Information Ltd. (Jul. 2001) (Document FP49).

Dialog File 351, Accession No. 3159675, Derwent WPI English language abstract for JP 63-20234, published 1988 (Document FP13).

Dialog File 351, Accession No. 3212225, Derwent WPI English language abstract for JP 56-104883, published 1981 (Document FP4).

Dialog File 351, Accession No. 3689403, Derwent WPI English language abstract for EP 123 700 A1, published 1984 (Document FP9) and DE 32 39 573 A1 (Document FP6), Derwent Information Ltd. (1983).

Dialog File 351, Accession No. 3710355, Derwent WPI English language abstract for DE 32 45 950 A1, published 1983 (Document FP7).

Dialog File 351, Accession No. 4789463, Derwent WPI English language abstract for European Patent No. EP 200 024 B1, published 1986 (Document FP10).

Dialog File 351, Accession No. 9527161, Derwent WPI English language abstract for EP 550 900 A1, published 1993 (Document FP28).

Carver, A.C. and Foley, K.M., "Complications of Cancer and Its Treatment, Management of Cancer Pain," in: *Cancer Medicine*, Holland, J.F., et al., eds., Williams & Wilkins, Baltimore, MD, pp. 2204-2223, USA (1997).

Office Action mailed Aug. 11, 2004, in U.S. Appl. No. 10/235,673, inventors Shao et al., filed Sep. 6, 2002.

Office Action mailed Mar. 24, 2005, in U.S. Appl. No. 10/235,673, inventors Shao et al., filed Sep. 6, 2002.

Office Action mailed Sep. 22, 2005, in U.S. Appl. No. 10/235,673, inventors Shao et al., filed Sep. 6, 2002.

Office Action mailed May 21, 2008, in U.S. Appl. No. 11/518,448, inventors Shao et al., filed Sep. 11, 2006.

Office Action mailed Nov. 7, 2008, in U.S. Appl. No. 11/518,448, inventors Shao et al., filed Sep. 11, 2006.

International Search Report for International Application No. PCT/US02/28298, European Patent Offiece, Netherlands, mailed on Jun. 12, 2002.

International Preliminary Examination Report for International Application No. PCT/US02/28298, European Patent Office, Germany, report completed on Nov. 27, 2003.

ARYL SUBSTITUTED PYRIDINES AND THE USE THEREOF

This application is a divisional of application Ser. No. 11/518,448, filed Sep. 11, 2006, now U.S. Pat. No. 7,579,367 B2, which is a divisional of application Ser. No. 10/235,673, filed Sep. 6, 2002, now U.S. Pat. No. 7,105,549 B2, which claims the priority benefit under 35 U.S.C. §119(e) of U.S. Provisional Application No. 60/317,526, filed Sep. 7, 2001, the entirety of which is incorporated by reference herein.

BACKGROUND OF THE INVENTION

1. Field of the Invention

This invention is in the field of medicinal chemistry. In particular, the invention relates to novel aryl substituted pyridines and the discovery that these compounds act as blockers of sodium ($Na^+$) channels.

2. Related Art

Several classes of therapeutically useful drugs, including local anesthetics such as lidocaine and bupivacaine, antiarrhythmics such as propafenone and amioclarone, and anticonvulsants such as lamotrigine, phenytoin and carbamazepine, have been shown to share a common mechanism of action by blocking or modulating $Na^+$ channel activity (Catterall, W. A., *Trends Pharmacol. Sci.* 8:57-65 (1987)). Each of these agents is believed to act by interfering with the rapid influx of $Na^+$ ions.

Recently, other $Na^+$ channel blockers such as BW619C89 and lifarizine have been shown to be neuroprotective in animal models of global and focal ischemia and are presently in clinical trials (Graham et al., *J. Pharmacol. Exp. Ther.* 269: 854-859 (1994); Brown et al., *British J. Pharmacol.* 115: 1425-1432 (1995)).

The neuroprotective activity of $Na^+$ channel blockers is due to their effectiveness in decreasing extracellular glutamate concentration during ischemia by inhibiting the release of this excitotoxic amino acid neurotransmitter. Studies have shown that unlike glutamate receptor antagonists, $Na^+$ channel blockers prevent hypoxic damage to mammalian white matter (Stys et al., *J. Neurosci.* 12:430-439 (1992)). Thus, they may offer advantages for treating certain types of strokes or neuronal trauma where damage to white matter tracts is prominent.

Another example of clinical use of a $Na^+$ channel blocker is riluzole. This drug has been shown to prolong survival in a subset of patients with ALS (Bensimm et al., *New Engl. J. Med.* 330:585-591 (1994)) and has subsequently been approved by the FDA for the treatment of ALS. In addition to the above-mentioned clinical uses, carbamazepine, lidocaine and phenytoin are occasionally used to treat neuropathic pain, such as from trigeminal neurologia, diabetic neuropathy and other forms of nerve damage (Taylor and Meldrum, *Trends Pharmacol. Sci.* 16:309-316 (1995)), and carbamazepine and lamotrigine have been used for the treatment of manic depression (Denicott et al., *J. Clin. Psychiatry* 55: 70-76 (1994)). Furthermore, based on a number of similarities between chronic pain and tinnitus, (Moller, A. R. *Am. J. Otol.* 18: 577-585 (1997); Tonndorf, *J. Hear. Res.* 28: 271-275 (1987)) it has been proposed that tinnitus should be viewed as a form of chronic pain sensation (Simpson, J. J. and Davies, E. W. *Tip.* 20: 12-18 (1999)). Indeed, lignocaine and carbamazepine have been shown to be efficacious in treating tinnitus (Majumdar, B. et al. *Clin. Otolaryngol.* 8: 175-180 (1983); Donaldson, I. *Laryngol. Otol.* 95: 947-951 (1981)).

It has been established that there are at least five to six sites on the voltage-sensitive $Na^+$ channels which bind neurotoxins specifically (Catterall, W. A., *Science* 242:50-61 (1988)). Studies have further revealed that therapeutic antiarrhythmics, anticonvulsants and local anesthetics whose actions are mediated by $Na^+$ channels, exert their action by interacting with the intracellular side of the $Na^+$ channel and allosterically inhibiting interaction with neurotoxin receptor site 2 (Catterall, W. A., *Ann. Rev. Pharmacol. Toxicol.* 10:15-43 (1980)).

JP 07076542 A2 describes liquid crystals and liquid crystal compositions comprising the following compounds:

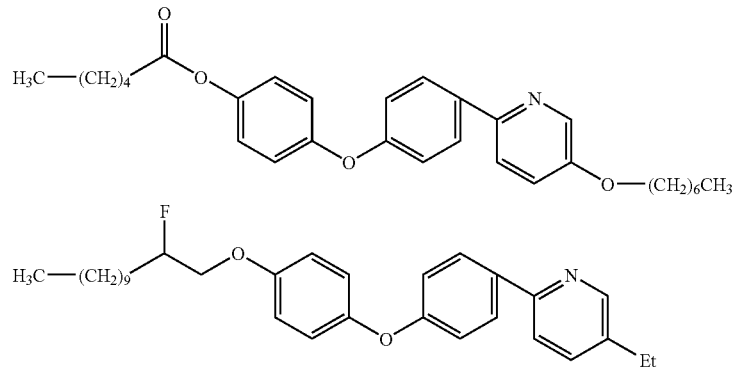

U.S. Pat. No. 5,403,934 describes the following intermediates for preparing antimalarials:

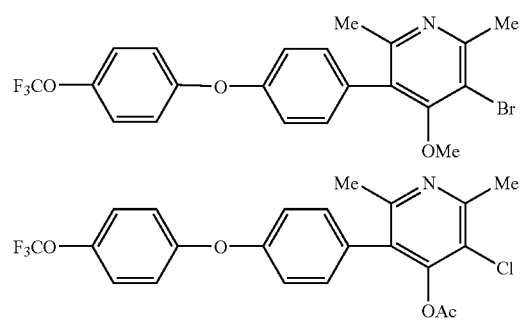

Liao et al. (*J. Heterocycl. Chem.* 13:1283-1288 (1976)) describe the following formula:

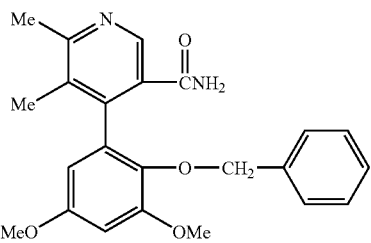

Salman (*Pharmazie* 54:178-183 (1999)) describes an antibacterial/antifungal compound of formula:

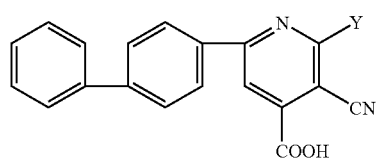

wherein Y is NHMe or OMe.

WO 9938829 describes a compound of formula:

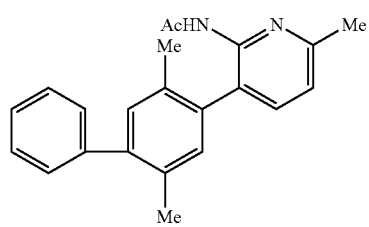

This compound is described to be useful as an immunosuppressant or an antiallegy agent.

Karamysheva et al. (*Mol. Cryst. Liq. Cryst.* 67:241-251 (1981)) describe compounds of formula:

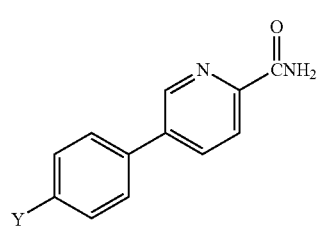

wherein Y is a straight chain $C_4$-$C_8$ alkyl or alkoxy.

DE 3245950 describes a compound of the following formula that is described to be useful as an antihypertensive:

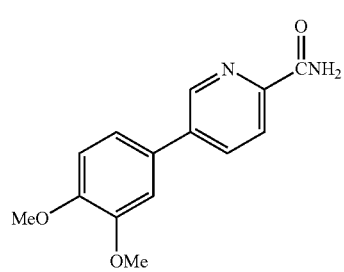

U.S. Pat. No. 4,920,119 describes several 2-phenyl-3-aminopyridine-4-carboxamide derivatives as reactants.

Troschuetz et al. (*Chem.-Ztg.* 114:321-322 (1990)) describe a compound of formula:

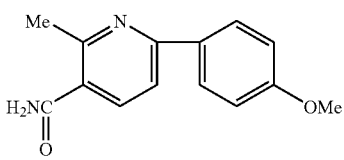

Goerlitzer et al. (*Arch. Pharm. (Weinheim, Ger.)* 325:357-359 (1992)) describe a compound of formula:

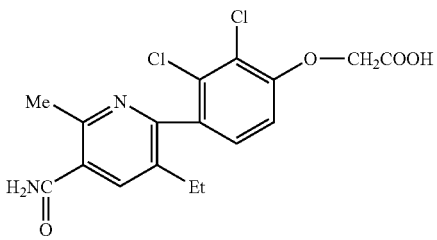

U.S. Pat. No. 5,389,632 describes the following compounds as reactants:

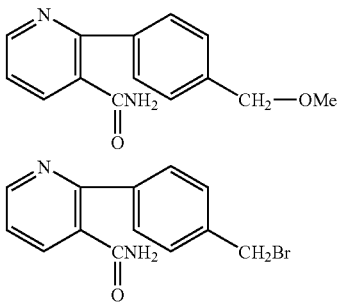

Goerlitzer et al. (*Pharmazie* 52:97-100 (1997)) describe the following compounds:

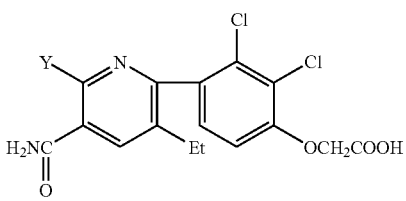

where Y is OMe or OEt.

Chambers et al. (*Bioorg. Med. Chem. Lett.* 7:739-744 (1997)) describe the following compounds as useful in the treatment of rheumatoid arthritis:

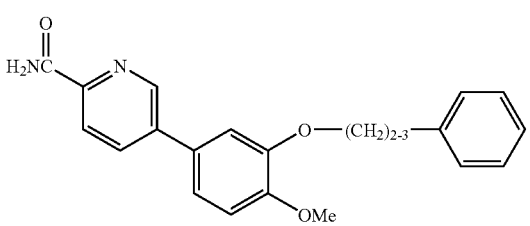

Reddy et al. (*Synth. Commun.* 27:2217-2222 (1997)) describe the following formula:

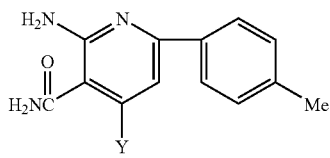

where Y is H or $CF_3$.

Rottlander et al. (*Synlett* (9):1084-1086 (1997)) describe 3-(4-methoxyphenyl)pyridine-4-carboxamide.

Singh et al. (*Indian J. Chem., Sect. B: Org Chem. Incl. Med. Chem.* 37B(5):517-520 (1998)) describe 2-amino-4-n-butoxy-5-(4-methoxyphenyl)pyridine-3-carboxamide.

SUMMARY OF THE INVENTION

The present invention is related to the discovery that aryl substituted pyridines represented by Formula I act as blockers of sodium ($Na^+$) channels.

The invention is also related with treating a disorder responsive to the blockade of sodium channels in a mammal suffering from excess activity of said channels by administering an effective amount of a compound of Formula I as described herein.

The present invention is also directed to the use of a compound of Formula I for the treatment of neuronal damage following global and focal ischemia, and for the treatment or prevention of neurodegenerative conditions such as amyotrophic lateral sclerosis (ALS), for the treatment of tinnitus, as antimanic depressants, as local anesthetics, as antiarrhythmics, as anticonvulsants and for the treatment or prevention of diabetic neuropathy and for the treatment of pain including both acute and chronic pain and migraine headache.

A number of compounds useful in the present invention have not been heretofor reported. Thus, one aspect of the present invention is directed to the novel aryl substituted pyridines of Formula I.

Another aspect of the present invention is directed to the novel compounds of Formula I as blockers of sodium channels.

A further aspect of the present invention is to provide a method for treating, preventing or ameliorating neuronal loss following global and focal ischemia; treating, preventing or ameliorating pain including acute and chronic pain, and neuropathic pain; treating, preventing or ameliorating convulsion and neurodegenerative conditions; treating, preventing or ameliorating manic depression; using as local anesthesics and anti-arrhythmics, and treating tinnitus by administering a compound of Formula I to a mammal in need of such treatment or use.

Also, an aspect of the present invention is to provide a pharmaceutical composition useful for treating disorders responsive to the blockade of sodium ion channels, containing an effective amount of a compound of Formula I in a mixture with one or more pharmaceutically acceptable carriers or diluents.

Further, the present invention is directed to $^3H$ and $^{14}C$ radiolabeled compounds of Formula I and their use as radioligands for their binding site on the sodium channel.

Additional embodiments and advantages of the invention will be set forth in part in the description that follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

The present invention arises out of the discovery that aryl substituted pyridines of Formula I act as blockers of $Na^+$ channels. In view of this discovery compounds of Formula I are useful for treating disorders responsive to the blockade of sodium ion channels.

The compounds useful in this aspect of the present invention are aryl substituted pyridines represented by Formula I:

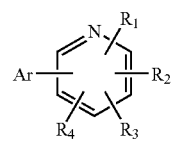

I or a pharmaceutically acceptable salt, prodrug or solvate thereof, wherein:

Ar is selected from the group consisting of $Ar_1$, $Ar_2$, $Ar_3$ and $Ar_4$, wherein

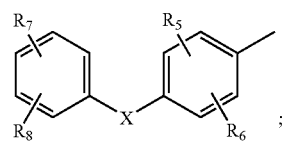

$Ar_1$ is

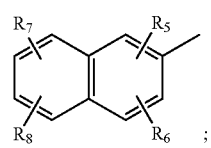

$Ar_2$ is

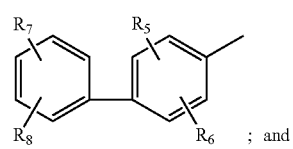
; and $Ar_3$ is

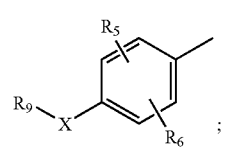
;

$Ar_4$ is $R_1$ is selected from the group consisting of an optionally substituted alkyl, amino, alkylthiol, $C(O)R_{10}$, $SO_2R_{10}$, $OC(O)NH_2$, 2-imidazolinyl, 2-imidazolyl, 3-pyrazolyl, 5-isoxazolyl, and 3-(1,2,4)-triazolyl;

$R_2$, $R_3$, and $R_4$ are independently selected from the group consisting of hydrogen, optionally substituted alkyl, alkenyl, or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino;

provided that 1) the pyridyl ring is other than 2,6-disubstituted with regard to Ar and $R_1$ or any of $R_2$-$R_4$ that is other than hydrogen; and 2) when Ar is $Ar_2$ or $Ar_3$, then $R_1$ is $C(O)R_{10}$;

3) when Ar is $Ar_4$, then $R_1$ is aminocarbonyl or an optionally substituted heterocycloalkylaminocarbonyl;

$R_5$, $R_6$, $R_7$, and $R_8$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, carbonylamido and alkylthiol;

$R_9$ is an optionally substituted alkyl;

$R_{10}$ is selected from the group consisting of alkyl, alkenyl, alkynyl, $OR_{11}$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, aralkyl, arylalkenyl, arylalkynyl, and arylalkylamino, all of which can be optionally substituted, provided that $R_{10}$ is not $OR_{11}$ when $R_1$ is $SO_2R_{10}$; wherein $R_{11}$ is selected from the group consisting of hydrogen, optionally substituted alkyl, and an alkali metal; and X is one of O, S, NH, or $CH_2$ when Ar is $Ar_1$; or X is one of O, S, NH, or absent (a covalent bond) when Ar is $Ar_4$.

Since the compounds of Formula I are blockers of sodium ($Na^+$) channels, a number of diseases and conditions mediated by sodium ion influx can be treated employing these compounds. Therefore, the invention is related to a method of treating, preventing or ameliorating neuronal loss associated with stroke, global and focal ischemia, CNS trauma, hypoglycemia and surgery, spinal cord trauma; as well as treating or ameliorating neurodegenerative diseases including Alzheimer's disease, amyotrophic lateral sclerosis, Parkinson's disease, treating or ameliorating anxiety, convulsions, glaucoma, migraine headache, and muscle spasm. The compounds of Formula I are also useful as antitinnitus agents, antimanic depressants, as local anesthetics, and as antiarrhythmics; as well as for treating, preventing or ameliorating pain including surgical, chronic and neuropathic pain. In each instance, the methods of the present invention require administering to an animal in need of such treatment an effective amount of a sodium channel blocker of the present invention, or a pharmaceutically acceptable salt or prodrug thereof.

Accordingly, compounds useful in the present invention are aryl substituted pyridines represented by Formula II:

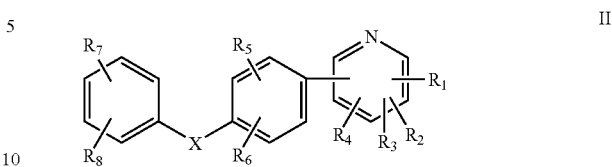

II or a pharmaceutically acceptable salt, prodrug or solvate thereof, wherein:

$R_1$ is selected from the group consisting of an optionally substituted alkyl, amino, alkylthiol, $C(O)R_{10}$, $SO_2R_{10}$, $OC(O)NH_2$, 2-imidazolinyl, 2-imidazolyl, 3-pyrazolyl, 5-isoxazolyl, and 3-(1,2,4)-triazolyl;

$R_2$, $R_3$, and $R_4$ are independently selected from the group consisting of hydrogen, optionally substituted alkyl, alkenyl, or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino;

provided that the pyridyl ring is other than 2,6-disubstituted with regard to the aryl radical and $R_1$ or any of $R_2$-$R_4$ that is other than hydrogen;

$R_5$, $R_6$, $R_7$, and $R_8$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, carbonylamido and alkylthiol; and $R_{10}$ is selected from the group consisting of alkyl, alkenyl, alkynyl, $OR_{11}$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, aralkyl, arylalkenyl, arylalkynyl, and arylalkylamino, all of which can be optionally substituted, provided that $R_{10}$ is not $OR_{11}$ when $R_1$ is $SO_2R_{10}$; wherein $R_{11}$ is selected from the group consisting of hydrogen, optionally substituted alkyl, and an alkali metal; and X is one of O, S, NH, or $CH_2$.

Another group of compounds useful in this aspect of the present invention are aryl substituted pyridines represented by the general Formula II, wherein $R_1$-$R_8$ and $R_{10}$-$R_{11}$ are as described above, with the proviso that when X is O, $R_5$, $R_6$ and $R_7$ are each hydrogen, and $R_1$ is an alkyl group, then $R_8$ is other than an optionally substituted alkoxy group.

Preferably, $R_1$ is selected from the group consisting of an alkyl optionally substituted by halogen or hydroxy, thiomethyl, $C(O)R_{10}$, $SO_2R_{10}$, 2-imidazolinyl, 2-imidazolyl, 3-pyrazolyl, and 5-isoxazolyl, wherein $R_{10}$ is selected from the group consisting of alkyl, alkenyl, $OR_{11}$, amino, alkylamino, dialkylamino, alkenylamino, dialkylaminoalkenyl, dialkylaminoalkylamino, and heterocycloalkylamino, all of which can be optionally substituted, provided that $R_{10}$ is not $OR_{11}$ when $R_1$ is $SO_2R_{10}$.

Preferably, $R_2$, $R_3$ and $R_4$ are independently selected from the group consisting of hydrogen, alkyl, alkenyl, alkynyl, aminoalkyl, amino, hydroxyalkyl, alkoxy, aminocarbonyl, alkylaminocarbonyl, arylaminocarbonyl, aralkylaminocarbonyl, alkylcarbonylamino, arylcarbonylamino, and aralkylcarbonylamino, more preferably hydrogen, alkyl, alkoxy, aminoalkyl and aminocarbonyl. Preferably both $R_3$ and $R_4$ are hydrogen.

Preferably, $R_5$, $R_6$, $R_7$, and $R_8$ are independently selected from the group consisting of hydrogen, alkyl, alkenyl, alkynyl, halogen, haloalkyl, hydroxyalkyl, hydroxy, nitro, amino, and cyano. More preferably, $R_5$, $R_6$, $R_7$ and $R_8$ are independently selected from the group consisting of hydrogen, alkyl, halogen, haloalkyl, and nitro. Preferred values of $R_5$-$R_8$ include hydrogen, halo, $C_1$-$C_6$ haloalkyl, $C_1$-$C_6$ alkyl, $C_2$-$C_6$ alkenyl, $C_2$-$C_6$ alkynyl, $C_1$-$C_6$ hydroxyalkyl, nitro, amino, ureido, cyano, $C_1$-$C_6$ acylamido, hydroxy, thiol, $C_1$-$C_6$ acyloxy, azido, $C_1$-$C_6$ alkoxy, or carboxy. The groups $R_5$-$R_8$ each take the place of a hydrogen atom that would otherwise be present in any position on the aryl ring to which the R group is attached. Especially preferred are compounds where $R_5$ and $R_6$ are both hydrogen, $R_7$ is hydrogen and $R_8$ is a fluoro in the para-position.

Preferably, $R_9$ is a branched alkyl group of $C_{3-10}$ carbon atoms, more preferably $C_{3-6}$ carbon atoms, optionally substituted with one or more of halogen, hydroxy, nitro, amino, cyano, and alkoxy.

Preferably, $R_{10}$ is selected from the group consisting of alkyl, alkenyl, $OR_{11}$, amino, alkylamino, dialkylamino, alkenylamino, dialkylaminoalkenyl, dialkylaminoalkylamino, and heterocycloalkylamino, preferably piperidinylethylamino, all of which can be optionally substituted, wherein $R_{11}$ is as defined above, provided that $R_{10}$ is not $OR_{11}$ when $R_1$ is $SO_2R_{10}$.

Preferably X is O or S, more preferably X is O.

In one aspect of the invention, preferred compounds falling within the scope of Formula II include compounds wherein X is O or S. In this aspect of the invention $R_1$ is preferably aminocarbonyl or heterocycloalkylaminocarbonyl, especially 2-(N-piperidinyl)ethylamino-carbonyl, and $R_2$, $R_3$, and $R_4$ each are preferably hydrogen. Preferred $R_5$-$R_8$ groups are as described above.

The invention also relates to aryl-substituted pyridines represented by Formula III:

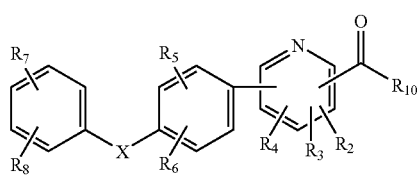

III or a pharmaceutically acceptable salt, prodrug or solvate thereof, wherein:

$R_2$-$R_8$, $R_{10}$ and X are defined previously with respect to Formulae I-II;

provided that the pyridyl ring is other than 2,6-disubstituted with regard to the aryl radical and —C(O)$R_{10}$ or any of $R_2$-$R_4$ that is other than hydrogen.

Preferred compounds falling within the scope of Formula III include compounds wherein $R_2$, $R_3$, and $R_4$ are hydrogen, $R_{10}$ is amino, and X is O and S. $R_5$ through $R_8$ have preferred values as described above for Formula II. Further, preferably $R_{10}$ is selected from the group consisting of alkyl, alkenyl, amino, alkylamino, dialkylamino, alkenylamino, dialkylaminoalkenyl, dialkylaminoalkylamino, and heterocycloalkylamino, preferably 2-(N-piperidinyl)ethylamino, all of which can be optionally substituted.

Further, compounds useful in the present invention are aryl substituted pyridines represented by Formula IV:

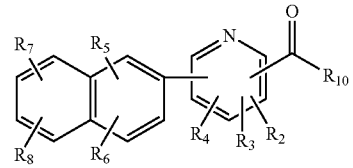

IV or a pharmaceutically acceptable salt, prodrug or solvate thereof, wherein:

$R_2$-$R_8$ are defined previously with respect to Formulae I-III, provided that the pyridyl ring is other than 2,6-disubstituted with regard to the naphthyl radical and —C(O)$R_{10}$ or any of $R_2$-$R_4$ that is other than hydrogen. $R_2$ through $R_8$ have preferred values as described above for Formula II. Preferably $R_2$-$R_4$ each are hydrogen.

Further, compounds useful in the present invention are aryl substituted pyridines represented by Formula V:

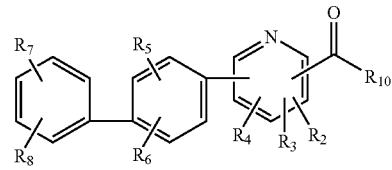

V or a pharmaceutically acceptable salt, prodrug or solvate thereof, wherein:

$R_2$-$R_8$ are defined previously with respect to Formulae I-III;

provided that the pyridyl ring is other than 2,6-disubstituted with regard to the biphenyl radical and —C(O)$R_{10}$ or any of $R_2$-$R_4$ that is other than hydrogen. $R_2$ through $R_8$ have preferred values as described above for Formula II. Preferably $R_2$-$R_4$ each are hydrogen.

Also, compounds useful in the present invention are aryl substituted pyridines represented by Formula VI:

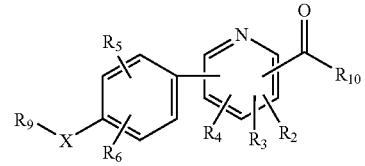

VI or a pharmaceutically acceptable salt, prodrug or solvate thereof, wherein:

$R_5$, $R_6$, and $R_9$ are defined previously with respect to Formulae I-II, X is one of O, S, NH, or absent, and $R_{10}$ is amino or heterocycloalkylamino;

provided that the pyridyl ring is other than 2,6-disubstituted with regard to the phenyl radical and —C(O)$R_{10}$.

Another group of compounds useful in this aspect of the present invention are aryl substituted pyridines represented by the general Formula VI, wherein $R_5$, $R_6$, $R_9$, and X are as described above, and $R_2$-$R_4$ each are hydrogen, with the proviso that when X is O or absent and $R_{10}$ is amino, then $R_9$ is not a straight chain alkyl group optionally mono-substituted with halogen, carboxy, alkoxy, an optionally substituted phenyl, or an optionally substituted aminocarbonyl.

Preferred compounds falling within the scope of Formula VI include compounds wherein X is O, S, or absent. Preferably, $R_9$ is a branched chain $C_{3-6}$ alkyl, more preferably $C_{3-4}$ alkyl, optionally substituted with one or more of halogen, especially fluoro or chloro, or trihalomethyl, especially trifluoromethyl. $R_5$ and $R_6$ have preferred values as described above for Formula II.

Exemplary preferred compounds that may be employed in this method of invention include, without limitation:
2-[4-(4-fluorophenoxy)phenyl]pyridine-3-carboxamide;
2-[4-(4-fluorophenoxy)phenyl]pyridine-4-carboxamide;
2-(4-phenoxyphenyl)pyridine-5-carboxamide;
2-(4-phenoxyphenyl)pyridine-4-carboxamide;
5-(4-phenoxyphenyl)pyridine-3-carboxamide
2-[4-(4-fluorophenoxy)phenyl]pyridine 5-carboxylic acid 2-(N-piperidinyl)ethylamide; and
5-[4-(4-fluorophenoxy)phenyl]pyridine 3-carboxylic acid 2-(N-piperidinyl)ethylamide;
or a pharmaceutically acceptable salt, prodrug or solvate thereof.

Additional useful compounds of the present invention include:
5-(2-naphthyl)pyridine-3-carboxamide;
2-(2-naphthyl)pyridine-5-carboxamide;
2-(4-phenylphenyl)pyridine-4-carboxamide; and
2-(4-phenylphenyl)pyridine-5-carboxamide;
or a pharmaceutically acceptable salt, prodrug or solvate thereof.

Further useful compounds of the invention include:
5-(4-tert-butylphenyl)pyridine-3-carboxamide;
2-(4-tert-butylphenyl)pyridine-4-carboxamide;
2-(4-tert-butylphenyl)pyridine-5-carboxamide
2-(4-i-propylphenyl)pyridine-4-carboxamide;
5-(4-thiomethylphenyl)pyridine-3-carboxamide;
2-(4-thiomethylphenyl)pyridine-5-carboxamide;
5-(4-trifluoromethoxyphenyl)pyridine-3-carboxamide;
2-(4-trifluoromethoxyphenyl)pyridine-5-carboxamide;
2-(4-trifluoromethoxyphenyl)pyridine-4-carboxamide;
5-(4-trifluoromethylphenyl)pyridine-3-carboxamide; and
2-(4-trifluoromethylphenyl)pyridine-5-carboxamide;
or a pharmaceutically acceptable salt, prodrug or solvate thereof.

Further compounds that may be employed in this method of invention include:
2-(4-n-butylphenyl)pyridine-4-carboxamide;
2-(4-methoxyphenyl)pyridine-4-carboxamide;
2-(4-ethoxyphenyl)pyridine-4-carboxamide;
5-(4-ethoxyphenyl)pyridine-3-carboxamide;
5-(4-methoxyphenyl)pyridine-3-carboxamide;
5-(4-n-butylphenyl)pyridine-3-carboxamide;
2-(4-ethoxyphenyl)pyridine-5-carboxamide;
2-(4-methoxyphenyl)pyridine-5-carboxamide;
2-(4-n-butylphenyl)pyridine-5-carboxamide;
or a pharmaceutically acceptable salt, prodrug or solvate thereof.

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful halo or halogen groups include fluorine, chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Useful alkenyl groups are $C_{2-6}$ alkenyl groups, preferably $C_{2-4}$ alkenyl. Typical $C_{2-4}$ alkenyl groups include ethenyl, propenyl, isopropenyl, butenyl, and sec-butenyl.

Useful alkynyl groups are $C_{2-6}$ alkynyl groups, preferably $C_{2-4}$ alkynyl. Typical $C_{2-4}$ alkynyl groups include ethynyl, propynyl, butynyl, and 2-butynyl groups.

Useful arylalkyl groups include any of the above-mentioned $C_{1-10}$ alkyl groups substituted by any of the above-mentioned $C_{6-14}$ aryl groups. Useful values include benzyl, phenethyl and naphthylmethyl.

Useful arylalkenyl groups include any of the above-mentioned $C_{2-4}$ alkenyl groups substituted by any of the above-mentioned $C_{6-14}$ aryl groups.

Useful arylalkynyl groups include any of the above-mentioned $C_{2-4}$ alkynyl groups substituted by any of the above-mentioned $C_{6-14}$ aryl groups. Useful values include phenylethynyl and phenylpropynyl.

Useful cycloalkylalkyl groups include any of the above-mentioned $C_{1-10}$ alkyl groups substituted by any of the above-mentioned cycloalkyl groups.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Useful hydroxyalkyl groups include $C_{1-10}$ alkyl groups substituted by hydroxy, e.g. hydroxymethyl, hydroxyethyl, hydroxypropyl and hydroxybutyl groups.

Useful alkoxy groups include oxygen substituted by one of the $C_{1-10}$ alkyl groups mentioned above.

Useful alkylthio groups include sulfur substituted by one of the $C_{1-10}$ alkyl groups mentioned above.

Useful acylamino groups are any acyl group, particularly $C_{2-6}$ alkanoyl or $C_{6-10}$ aryl($C_{2-6}$)alkanoyl attached to an amino nitrogen, e.g. acetamido, propionamido, butanoylamido, pentanoylamido, hexanoylamido, and benzoyl.

Useful acyloxy groups are any $C_{1-6}$ acyl (alkanoyl) attached to an oxy (—O—) group, e.g. acetoxy, propionoyloxy, butanoyloxy, pentanoyloxy, hexanoyloxy and the like.

The term heterocyclic is used herein to mean saturated or wholly or partially unsaturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Examples include, but are not limited to, pyrrolidine, piperidine, piperazine, morpholine, imidazoline, pyrazolidine, benzodiazepines, and the like.

Useful heterocycloalkyl groups include any of the above-mentioned $C_{1-10}$ alkyl groups substituted by any of the above-mentioned heterocyclic groups.

Useful heterocycloalkylamino groups include any of the above-mentioned heterocycloalkyl groups attached to an amino nitrogen, such as N-piperidinylethylamino, especially, 2-(N-piperidinyl)ethylamino.

Useful alkylamino and dialkylamino groups are —NHR$_{12}$ and —NR$_{12}$R$_{13}$, wherein R$_{12}$ and R$_{13}$ are C$_{1-10}$ alkyl groups.

Useful dialkylaminoalkyl groups include any of the above-mentioned C$_{1-10}$ alkyl groups substituted by any of the above-mentioned dialkylamino groups.

Useful dialkylaminoalkylamino groups include any of the above-mentioned dialkylaminoalkyl groups attached to an amino nitrogen, such as dimethylaminoethylamino.

Aminocarbonyl group is —C(O)NH$_2$.

Useful alkylaminocarbonyl groups are carbonyl groups substituted by —NHR$_{12}$ and —NR$_{12}$R$_{13}$, wherein R$_{12}$ and R$_{13}$ are C$_{1-10}$ alkyl groups.

Useful alkylthiol groups include any of the above-mentioned C$_{1-10}$ alkyl groups substituted by a —SH group.

A carboxy group is —COOH.

An azido group is —N$_3$.

An ureido group is —NH—C(O)—NH$_2$.

An amino group is —NH$_2$.

An amide group is an organic radical having —NHC(O)— as a functional group.

Optional substituents on R$_1$-R$_{11}$ include any one of halo, halo(C$_{1-6}$) alkyl, aryl, heterocycle, cycloalkyl, C$_{1-6}$ alkyl, C$_{2-6}$ alkenyl, C$_{2-6}$ alkynyl, aryl(C$_{1-6}$)alkyl, aryl(C$_{2-6}$)alkenyl, aryl(C$_{2-6}$)alkynyl, cycloalkyl(C$_{1-6}$)alkyl, heterocyclo(C$_{1-6}$) alkyl, hydroxy(C$_{1-6}$)alkyl, amino(C$_{1-6}$)alkyl, carboxy(C$_{1-6}$) alkyl, alkoxy(C$_{1-6}$)alkyl, nitro, amino, ureido, cyano, acylamino, hydroxy, thiol, acyloxy, azido, alkoxy, carboxy, aminocarbonyl, and C$_{1-6}$ alkylthiol groups mentioned above. Preferred optional substituents include: halo, halo(C$_{1-6}$)alkyl, hydroxy(C$_{1-6}$)alkyl, amino(C$_{1-6}$)alkyl, hydroxy, nitro, C$_{1-6}$ alkyl, alkoxy and amino.

The invention disclosed herein is also meant to encompass prodrugs of the disclosed compounds. Prodrugs are considered to be any covalently bonded carriers which release the active parent drug in vivo.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Some of the compounds disclosed herein may contain one or more asymmetric centers and may thus give rise to enantiomers, diastereomers, and other stereoisomeric forms. The present invention is also meant to encompass all such possible forms, as well as their racemic and resolved forms and mixtures thereof. The individual enantiomers may be separated according to methods that are well known to those of ordinary skill in the art. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

The invention disclosed is also meant to encompass all pharmaceutically acceptable salts thereof of the disclosed compounds. Examples of pharmaceutically acceptable addition salts include inorganic and organic acid addition salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Examples of prodrugs include esters or amides of Formulae I-VI with any of R$_2$-R$_8$ as hydroxyalkyl or aminoalkyl, and these may be prepared by reacting such compounds with anhydrides such as succinic anhydride.

The invention is also directed to a method for treating disorders responsive to the blockade of sodium channels in animals suffering thereof. Particular preferred embodiments of the aryl substituted pyridyl compounds for use in method of this invention are represented by previously defined Formulae I-VI.

The compounds of this invention may be prepared using methods known to those skilled in the art. For example, 2,5-disubstituted pyridine amides can be prepared according to Scheme 1 as follows:

SCHEME 1
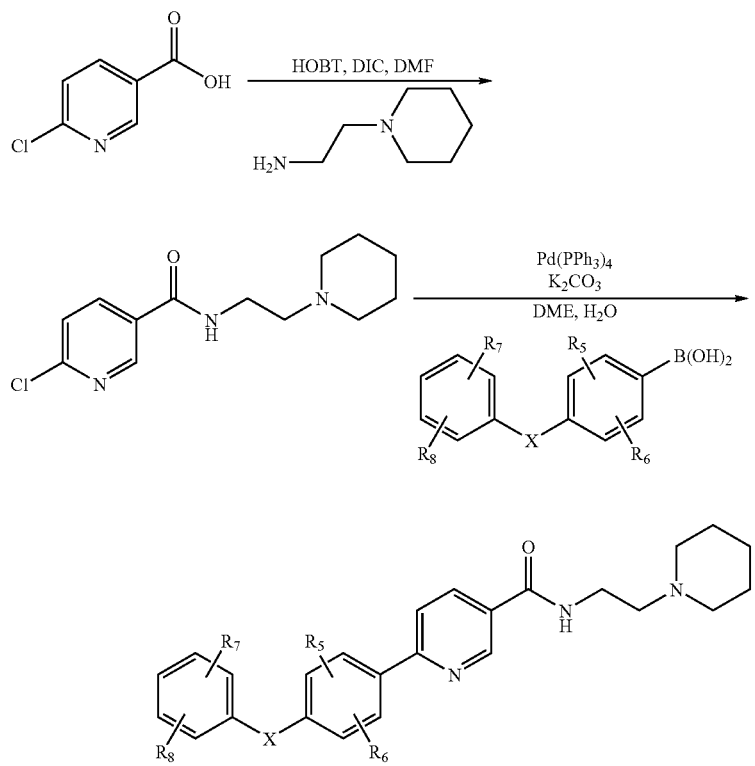
Further, 3,5-disubstituted pyridine amides can be prepared according to Scheme 2 as follows:
SCHEME 2
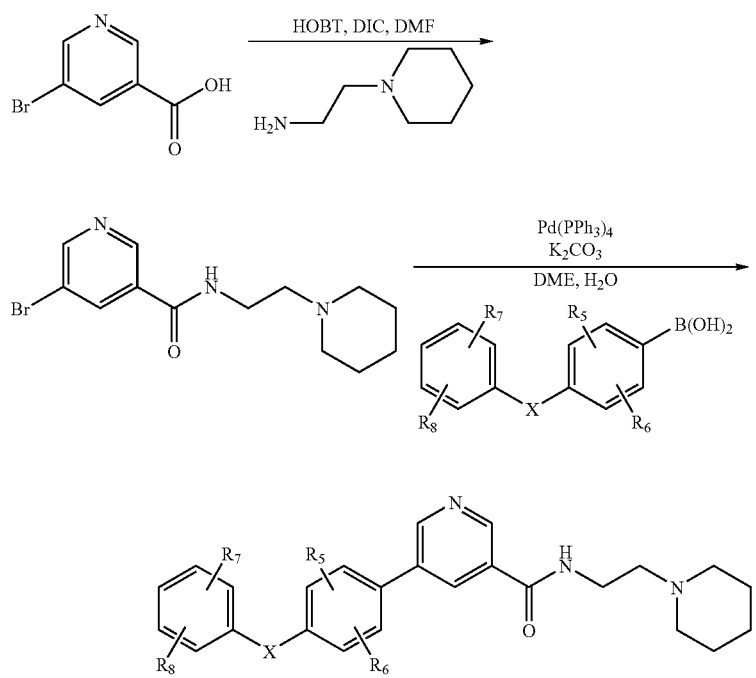

2,4-Disubstituted pyridine amides can be prepared, for example, as follows in Scheme 3:

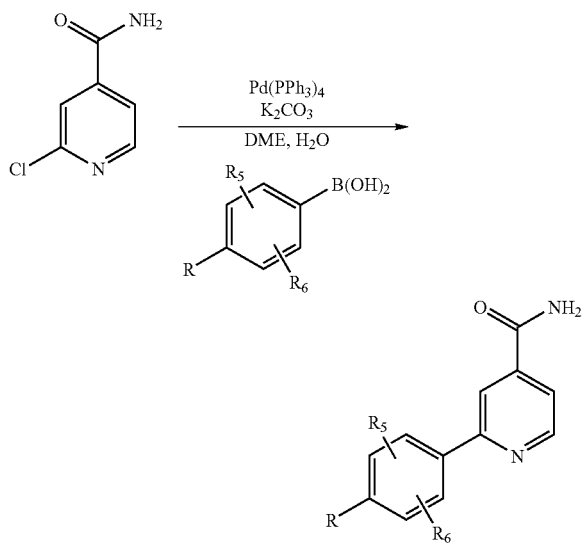

wherein R is, e.g., OPh, tert-butyl, Ph, n-butyl, i-Pr, OCF$_3$, OMe or OEt.

2,3-Distributed pyridine amides can be prepared, for example, as shown in Scheme 4.

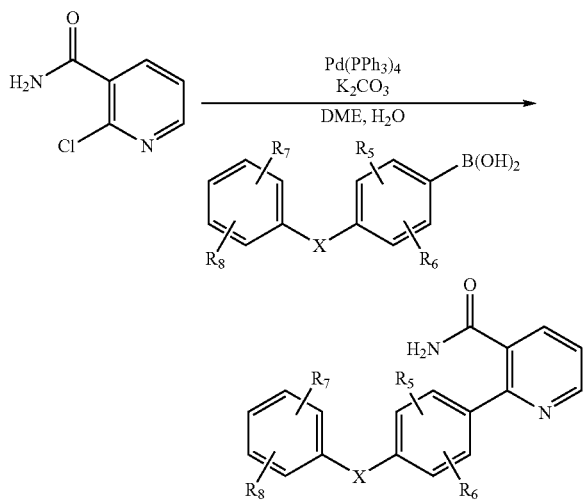

The invention is also directed to $^3$H and $^{14}$C radiolabeled compounds of Formula I and their use as radioligands for their binding site on the sodium channel. For example, one use of the labeled compounds of the invention is the characterization of specific receptor binding. Another use of the labeled compounds of the invention is an alternative to animal testing for the evaluation of structure-activity relationships. The receptor assay is performed at a fixed concentration of a labeled compound of Formula I and at increasing concentrations of a test compound in a competition assay.

Tritiated compounds of Formula I can be prepared by introducing tritium into the compound of Formula I by, for example, catalytic dehalogenation with tritium. This method includes reacting a suitably halogen-substituted precursor of a compound of Formula I with tritium gas in the presence of a suitable catalyst, for example Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6. $^{14}$C-labeled compounds can be prepared by employing starting materials having a $^{14}$C carbon.

The compounds of the present invention were assessed by electrophysiological assays in dissociated hippocampal neurons for sodium channel blocker activity. These compounds also could be assayed for binding to the neuronal voltage-dependent sodium channel using rat forebrain membranes and [$^3$H]BTX-B.

Sodium channels are large transmembrane proteins that are expressed in various tissues. They are voltage sensitive channels and are responsible for the rapid increase of Na$^+$ permeability in response to depolarization associated with the action potential in many excitable cells including muscle, nerve and cardiac cells.

One aspect of the present invention is the discovery of the mechanism of action of the compounds herein described as specific Na$^+$ channel blockers. Based upon the discovery of this mechanism, these compounds are contemplated to be useful in treating or preventing neuronal loss due to focal or global ischemia, and in treating or preventing neurodegenerative disorders including ALS, anxiety, and epilepsy. They are also expected to be effective in treating, preventing or ameliorating neuropathic pain, surgical pain, chronic pain and tinnitus. The compounds are also expected to be useful as antiarrhythmics, anesthetics and antimanic depressants.

The present invention is directed to compounds of Formulae I-VI that are blockers of voltage-sensitive sodium channels. According to the present invention, those compounds having preferred sodium channel blocking properties exhibit an IC$_{50}$ of about 100 µM or less in the electrophysiological assay described herein. Preferably, the compounds of the present invention exhibit an IC$_{50}$ of 10 µM or less. Most preferably, the compounds of the present invention exhibit an IC$_{50}$ of about 1.0 µM or less. Substituted heteroaryl compounds of the present invention may be tested for their Na$^+$ channel blocking activity by the following electrophysiological and binding assays.

Electrophysiological Assay:

Electrophysiological Assay was used to measure potencies of compounds of the present invention rBIIa/beta 1 sodium channels expressed in *Xenopus* oocytes.

Preparation of cRNA encoding cloned rat brain type IIa (rBIIa) and beta 1 (β1): cDNA clones encoding the rat brain beta 1 subunit were cloned in house using standard methods, and mRNA were prepared by standard methods. mRNA encoding rBIIa was provided by Dr. A. Golden (UC Irvine). The mRNAs were diluted and stored at −80° C. in 1 µL aliquots until injection.

Preparation of oocytes: Mature female *Xenopus laevis* were anaesthetized (20-40 min) using 0.15% 3-aminobenzoic acid ethyl ester (MS-222) following established procedures (Woodward, R. M., et al., *Mol. Pharmacol.* 41:89-103 (1992)).

Two to six ovarian lobes were surgically removed. Oocytes at developmental stages V-VI were dissected from the ovary, oocytes were still surrounded by enveloping ovarian tissues. Oocytes were defolliculated on the day of surgery by treatment with collagenase (0.5 mg/mL Sigma Type I, or Boehringer Mannheim Type A, for 0.5-1 hr). Treated oocytes were vortexed to dislodge epithelia, washed repeatedly and stored in Barth's medium containing 88 mM NaCl, 1 mM KCl, 0.41 mM $CaCl_2$, 0.33 mM $Ca(NO_3)_2$, 0.82 mM $MgSO_4$, 2.4 mM $NaHCO_3$, 5 mM HEPES, pH 7.4 adjusted with 0.1 mg/mL gentamycin sulphate.

Micro-injection of oocytes: Defolliculated oocytes were micro-injected using a Nanoject injection system (Drummond Scientific Co., Broomall, Pa.). Injection pipettes were beveled to minimize clogging. Tip diameter of injection pipettes was 15-35 µm. Oocytes were microinjected with approximately 50 nL 1:10 ratio mixtures of cRNAs for rBIIa and beta 1 respectively.

Electrophysiology: Membrane current responses were recorded in frog Ringer solution containing 115 mM NaCl, 2 mM KCl, 1.8 mM $CaCl_2$, 5 mM HEPES, pH 7.4. Electrical recordings were made using a conventional two-electrode voltage clamp (Dagan TEV-200) over periods ranging between 1-7 days following injection. The recording chamber was a simple gravity fed flow-through chamber (volume 100-500 mL depending on adjustment of aspirator). Oocytes were placed in the recording chamber, impaled with electrodes and continuously perfused (5-15 mL $min^{-1}$) with frog Ringer's solution. The tested compounds were applied by bath perfusion.

Voltage protocols for evoking sodium channel currents: The standard holding potential for whole oocyte clamp was −120 mV. Standard current-voltage relationships were elicited by 40 ms depolarizing steps starting from −60 mV to +50 mV in 10 mV increments. Peak currents were measured as the maximum negative current after depolarizing voltage steps. The voltage from maximum current response was noted and used for the next voltage protocol.

The purpose was to find compounds that are state dependent modifiers of neuronal sodium channels. Preferably, the compounds have a low affinity for the rested/closed state of the channel, but a high affinity for the inactivated state. The following voltage protocol was used to measure a compounds affinity for the inactivated state. Oocytes were held at a holding potential of −120 mV. At this membrane voltage, nearly all of the channels would be in the closed state. Then a 4 second depolarization was made to the voltage where the maximum current was elicited. At the end of this depolarization, nearly all the channels would be in the inactivated state. A 10 ms hyperpolarizing step was then made in order to remove some channels from the inactivated state. A final depolarizing test pulse was used to assay the sodium current after this prolonged depolarization (see analysis below). Sodium currents were measured at this test pulse before and after the application of the tested compound. Data was acquired using pClamp 8.0 software and analyzed with clampfit software (Axon instruments).

Data analysis: Apparent inhibition constants ($K_i$ values) for antagonists were determined from single point inhibition data using the following equation (a generalized form of the Cheng-Prusoff equation) (Leff, P. and I. G. Dougall, *TiPS* 14:110-112 (1993)).

$$K_i = (FR/1-FR)*[drug] \qquad \text{Eq. 1}$$

Where FR is the fractional response and is defined as sodium current elicited from the final depolarizing test pulse prior to application of the drug divided by the sodium current measured in the presence of the drug. [drug] is the concentration of the drug used.

Drugs: Drugs were initially made up at concentrations of 2-10 mM in DMSO. Dilutions were then made to generate a series of DMSO stocks over the range 0.3 µM to 10 mM—depending upon the potency of the compound. Working solutions were made by 1000-3000 fold dilution of stocks into Ringer. At these dilutions DMSO alone had little or no measurable effects on membrane current responses. DMSO stocks of drugs were stored in the dark at 4° C. Ringer solutions of drugs were made up fresh each day of use.

In Vitro Binding Assay:

The ability of compounds of the present invention to modulate either site 1 or site 2 of the $Na^+$ channel was determined following the procedures fully described in Yasushi, *J. Biol. Chem.* 261:6149-6152 (1986) and Creveling, *Mol. Pharmacol.* 23:350-358 (1983), respectively. Rat forebrain membranes were used as sources of $Na^+$ channel proteins. The binding assays were conducted in 130 µM choline chloride at 37° C. for 60-minute incubation with [$^3$H] saxitoxin and [$^3$H] batrachotoxin as radioligands for site 1 and site 2, respectively.

In Vivo Pharmacology:

The compounds of the present invention may be tested for in vivo anticonvulsant activity after i.v., p.o. or i.p. injection using a number of anticonvulsant tests in mice, including the maximum electroshock seizure test (MES). Maximum electroshock seizures were induced in male NSA mice weighing between 15-20 g and male Sprague-Dawley rats weighing between 200-225 g by application of current (50 mA, 60 pulses/sec, 0.8 msec pulse width, 1 sec duration, D.C., mice; 99 mA, 125 pulses/sec, 0.8 msec pulse width, 2 sec duration, D.C., rats) using a Ugo Basile ECT device (Model 7801). Mice were restrained by gripping the loose skin on their dorsal surface and saline-coated corneal electrodes were held lightly against the two corneae. Rats were allowed free movement on the bench top and ear-clip electrodes were used. Current was applied and animals were observed for a period of up to 30 seconds for the occurrence of a tonic hindlimb extensor response. A tonic seizure was defined as a hindlimb extension in excess of 90 degrees from the plane of the body. Results were treated in a quantal manner.

The compounds may be tested for their antinociceptive activity in the formalin model as described in Hunskaar, S., O. B. Fasmer, and K. Hole, *J. Neurosci. Methods* 14: 69-76 (1985). Male Swiss Webster NIH mice (20-30 g; Harlan, San Diego, Calif.) were used in all experiments. Food was withdrawn on the day of experiment. Mice were placed in Plexiglass jars for at least 1 hour to accommodate to the environment. Following the accommodation period mice were weighed and given either the compound of interest administered i.p. or p.o., or the appropriate volume of vehicle (10% Tween-80). Fifteen minutes after the i.p. dosing, and 30 minutes after the p.o. dosing mice were injected with formalin (20 µL of 5% formaldehyde solution in saline) into the dorsal surface of the right hind paw. Mice were transferred to the Plexiglass jars and monitored for the amount of time spent licking or biting the injected paw. Periods of licking and biting were recorded in 5 minute intervals for 1 hour after the formalin injection. All experiments were done in a blinded manner during the light cycle. The early phase of the formalin response was measured as licking/biting between 0-5 minutes, and the late phase was measured from 15-50 minutes. Differences between vehicle and drug treated groups were analyzed by one-way analysis of variance (ANOVA). A P value $\leq 0.05$ was considered significant. Having activity in blocking the acute and second phase of formalin-induced paw-licking activity, the compounds are considered to be efficacious for acute and chronic pain.

The compounds may be tested for their potential for the treatment of chronic pain (antiallodynic and antihyperalgesic activities) in the Chung model of peripheral neuropathy. Male Sprague-Dawley rats weighing between 200-225 g were anesthetized with halothane (1-3% in a mixture of 70% air and 30% oxygen) and their body temperature controlled during anesthesia through use of a homeothermic blanket. A 2-cm dorsal midline incision was then made at the L5 and L6 level and the para-vertibral muscle groups retracted bilaterally. L5 and L6 spinal nerves were then be exposed, isolated, and tightly ligated with 6-0 silk suture. A sham operation was performed exposing the contralateral L5 and L6 spinal nerves as a negative control.

Tactile Allodynia. Rats were transferred to an elevated testing cage with a wire mesh floor and allowed to acclimate for five to ten minutes. A series of Semmes-Weinstein monofilaments were applied to the plantar surface of the hindpaw to determine the animal's withdrawal threshold. The first filament used possessed a buckling weight of 9.1 gms (0.96 log value) and was applied up to five times to see if it elicited a withdrawal response. If the animal had a withdrawal response then the next lightest filament in the series would be applied up to five times to determine if it could elicit a response. This procedure was repeated with subsequent lesser filaments until there was no response and the lightest filament that elicited a response was recorded. If the animal did not have a withdrawal response from the initial 9.1 gms filament then subsequent filaments of increased weight were applied until a filament elicited a response and this filament was then recorded. For each animal, three measurements were made at every time point to produce an average withdrawal threshold determination. Tests were performed prior to and at 1, 2, 4 and 24 hours post drug administration. Tactile allodynia and mechanical hyperalgesia tests were conducted concurrently.

Mechanical Hyperalgesia. Rats were transferred to an elevated testing cage with a wire mesh floor and allowed to acclimate for five to ten minutes. A slightly blunted needle was touched to the plantar surface of the hindpaw causing a dimpling of the skin without penetrating the skin. Administration of the needle to control paws typically produced a quick flinching reaction, too short to be timed with a stopwatch and arbitrarily given a withdrawal time of 0.5 second. The operated side paw of neuropathic animals exhibited an exaggerated withdrawal response to the blunted needle. A maximum withdrawal time of ten seconds was used as a cutoff time. Withdrawal times for both paws of the animals were measured three times at each time point with a five-minute recovery period between applications. The three measures were used to generate an average withdrawal time for each time point. Tactile allodynia and mechanical hyperalgesia tests were conducted concurrently.

The compounds may be tested for their neuroprotective activity after focal and global ischemia produced in rats or gerbils according to the procedures described in Buchan et al. (*Stroke, Suppl.* 148-152 (1993)) and Sheardown et al. (*Eur. J Pharmacol.* 236:347-353 (1993)) and Graham et al. (*J. Pharmacol. Exp. Therap.* 276:1-4 (1996)).

The compounds may be tested for their neuroprotective activity after traumatic spinal cord injury according to the procedures described in Wrathall et al. (*Exp. Neurology* 137: 119-126 (1996)) and Iwasaki et al. (*J. Neuro Sci.* 134:21-25 (1995)).

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for epilepsy, neurodegenerative diseases, anesthetic, arrhythmia, manic depression, and pain. For intramuscular injection, the dose is generally about one-half of the oral dose.

In the method of treatment or prevention of neuronal loss in global and focal ischemia, brain and spinal cord trauma, hypoxia, hypoglycemia, status epilepsy and surgery, the compound can be administrated by intravenous injection at a dose of about 0.025 to about 10 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular heteroaryl compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the heteroaryl compound of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal that may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings that, if desired, are resistant to gastric juices. For this purpose, concentrated saccharide solutions may be used, which may optionally contain gum arabic, talc, polyvinyl pyrrolidone, poly-ethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally, include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension, and include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

Example 1

2-[4-(4-Fluorophenoxy)phenyl]pyridine 5-carboxylic acid 2-(N-piperidinyl)ethylamide (3)

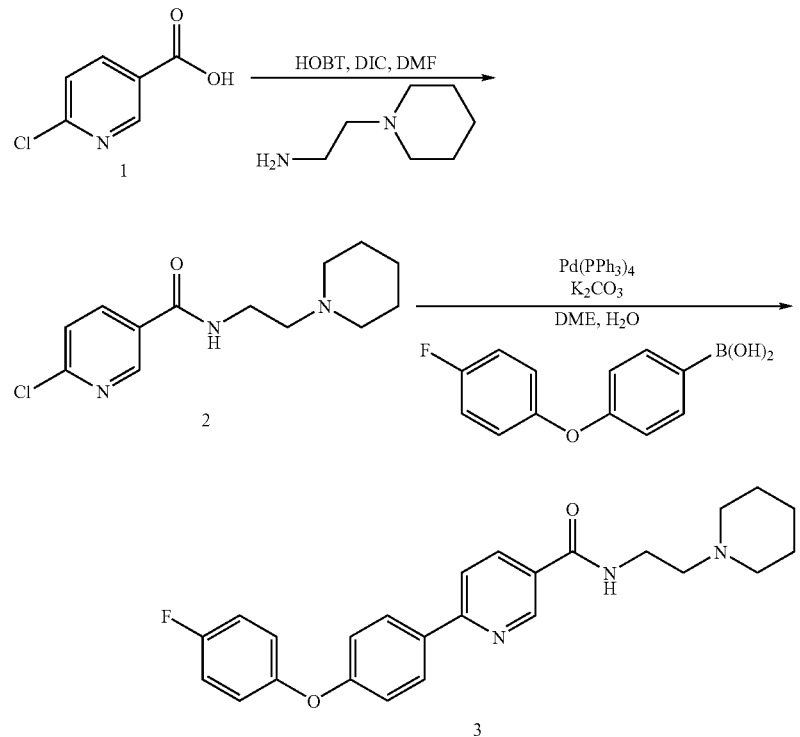

a) 2-Chloropyridine-5-carboxylic acid 2-(N-piperidinyl)-ethylamide (2): To a solution of 6-chloronicotinic acid (1) (3.9 g, 24.8 mmol) and 1-(2-aminoethyl)-piperidine (3.3 g, 26.0 mmol) in DMF was added N-hydroxybenzotriazole (HOBt) (3.4 g, 24.8 mmol) and 5-(3,4-dimethyl-1-triazenyl)-1H-imidazole-4-carboxamide (DIC) (3.1 g, 24.8 mmol). The reaction mixture was allowed to stir 24 hours at ambient temperature. The reaction mixture was diluted with dichloromethane, and water was then added. The phases were separated, and the aqueous phase was extracted twice with dichloromethane. The combined organic phases were dried over sodium sulfate. The solution was filtered and concentrated to give compound 2 as a pale-yellow solid. Purification of compound 2 was then carried out by silica gel chromatography.

b) 2-[4-(4-Fluorophenoxy)phenyl]pyridine 5-carboxylic acid 2-(N-piperidinyl)ethylamide (3): To a solution of compound 2 (536 mg, 2.0 mmol) in 1,2-dimethoxyethane (6 mL) was added 4-(4-fluorophenoxy)phenyl boronic acid (557 mg, 2.4 mmol), followed by water (2 mL) and potassium carbonate (746 mg, 5.4 mmol). Pd(PPh$_3$)$_4$ (92 mg, 0.08 mmol) was added to this mixture and the reaction mixture was heated at 85° C. for 16 hours under an argon atmosphere. The reaction mixture was allowed to return to ambient temperature, and the phases were separated. The aqueous phase was extracted three times with ethyl acetate, and the combined organic phases were dried over sodium sulfate. The solution was filtered, concentrated, and then filtered over a bed of florisil to give crude compound 3. Purification of compound 3 was then carried out by silica gel chromatography. $^1$H NMR (400 MHz, CDCl$_3$): δ 1.27 (bs, 2H), 1.50-1.66 (m, 4H), 2.48 (bs, 4H), 2.61 (t, 2H, J=6.0 Hz), 3.58 (t, 2H, J=5.8 Hz), 7.04-7.11 (m, 6H), 7.21 (bs, 1H), 7.78 (d, 1H, J=8.3 Hz), 8.03 (d, 2H, J=8.8 Hz), 8.22 (d, 1H, J=8.3 Hz), 9.04 (s, 1H).

The following compound was prepared similarly except that 5-bromonicotinic acid was used instead of 6-chloronicotinic acid in step a):

5-[4-(4-fluorophenoxy)phenyl]pyridine 3-carboxylic acid 2-(N-piperidinyl)ethylamide (6): $^1$H NMR (400 MHz, CDCl$_3$): δ 1.48 (bs, 2H), 1.59-1.64 (m, 4H), 2.47 (bs, 4H), 2.60 (t, 2H, J=6.1 Hz), 3.58 (t, 2H, J=5.7 Hz), 7.03-7.11 (m, 6H), 7.32 (bs, 1H), 7.59 (d, 2H, J=8.6 Hz), 8.35 (t, 1H, J=2.2 Hz), 8.92 (d, 2H, J=2.1 Hz).

Example 2

2-(4-Phenoxyphenyl)pyridine-4-carboxamide (8a)

2-(4-tert-Butylphenyl)pyridine-4-carboxamide (8b)

2-(4-Phenylphenyl)pyridine-4-carboxamide (8c)

2-(4-n-Butylphenyl)pyridine-4-carboxamide (8d)

2-(4-i-Propylphenyl)pyridine-4-carboxamide (8e)

2-(4-Trifluoromethoxyphenyl)pyridine-4-carboxamide (8f)

2-(4-Methoxyphenyl)pyridine-4-carboxamide (8g)

2-(4-Ethoxyphenyl)pyridine-4-carboxamide (8h)

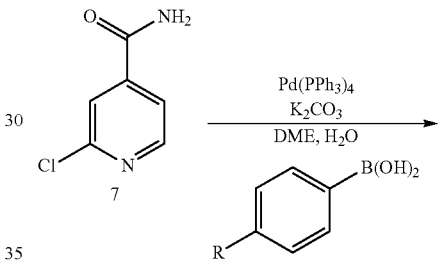

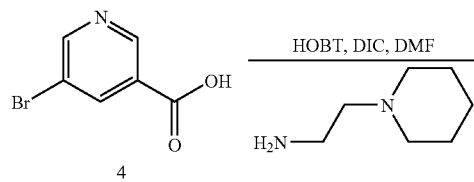

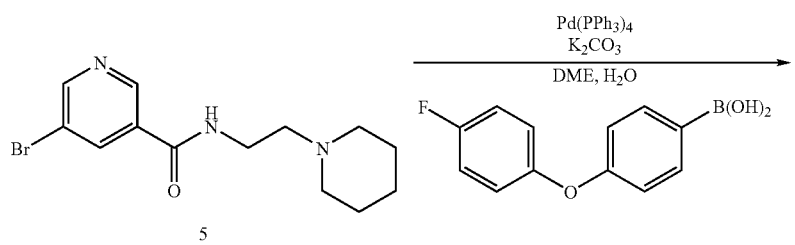

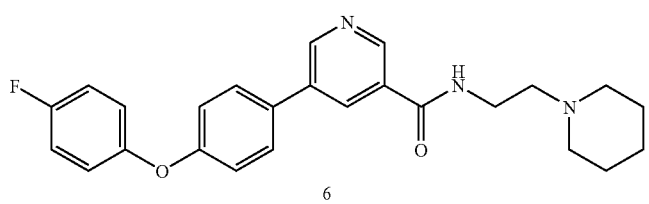

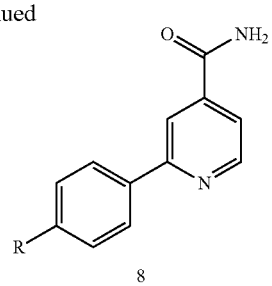

a R = OPh
b R = tert-butyl
c R = Ph
d R = n-butyl
e R = i-Pr
f R = OCF₃
g R = OMe
h R = OEt Compounds 8a-8h: To a solution of compound 7 (536 mg, 2.0 mmol) in 1,2-dimethoxyethane (6 mL) was added the appropriate phenyl boronic acid (2.4 mmol), followed by water (2 mL) and potassium carbonate (746 mg, 5.4 mmol). Pd(PPh₃)₄ (92 mg, 0.08 mmol) was added to this mixture, and the reaction mixture was heated at 85° C. for 16 hours under an argon atmosphere. The reaction mixture was allowed to return to ambient temperature, and the phases were separated. The aqueous phase was extracted three times with ethyl acetate, and the combined organic phases were dried over sodium sulfate. The solution was filtered, concentrated, and then filtered over a bed of florisil to give crude compounds 8a-8h. Purification of compounds 8a-8h was then carried out by silica gel chromatography.

2-(4-Phenoxyphenyl)pyridine-4-carboxamide (8a): ¹H NMR (400 MHz, CD₃OD): δ 7.03-7.15 (m, 5H), 7.33-7.41 (m, 2H), 7.62 (d, 1H, J=5.1 Hz), 7.95 (d, 2H, J=8.7 Hz), 8.14 (s, 1H), 8.69 (d, 1H, J=5.1 Hz).

2-(4-tert-Butylphenyl)pyridine-4-carboxamide (8b): ¹H NMR (400 MHz, CD₃OD): δ 1.41 (s, 9H), 7.57 (d, 2H, J=8.6 Hz), 7.66 (dd, 1H, J=1.6, 5.1 Hz), 7.98 (d, 2H, J=8.6 Hz), 8.20-8.21 (m, 1H), 8.77-8.78 (m, 1H).

2-(4-Phenylphenyl)pyridine-4-carboxamide (8c): ¹H NMR (400 MHz, CD₃OD): δ 7.35-7.48 (m, 4H), 7.64-7.75 (m, 5H), 8.08 (d, 2H, J=8.4 Hz), 8.25 (s, 1H), 8.75 (d, 1H, J=5.2 Hz).

2-(4-n-Butylphenyl)pyridine-4-carboxamide (8d): ¹H NMR (400 MHz, CD₃OD): δ 0.95 (t, 3H, J=7.3 Hz), 1.37-1.42 (m, 2H), 1.62-1.67 (m, 2H), 2.69 (t, 2H, J=7.6 Hz), 7.33 (d, 2H, J=8.3 Hz), 7.68 (dd, 1H, J=1.6, 5.2 Hz), 7.91 (d, 1H, J=8.3 Hz), 8.20 (s, 1H), 8.72 (d, 1H, J=5.1 Hz).

2-(4-i-Propylphenyl)pyridine-4-carboxamide (8e): ¹H NMR (400 MHz, CD₃OD): δ 1.30 (d, 6H, J=6.9 Hz), 2.93-3.06 (m, 1H), 7.38 (d, 2H, J=8.2 Hz), 7.67-7.69 (m, 1H), 7.93 (d, 2H, J=8.3 Hz) 8.21 (s, 1H), 8.73 (d, 2H, J=5.1 Hz).

2-(4-Trifluoromethoxyphenyl)pyridine-4-carboxamide (8f): ¹H NMR (400 MHz, CD₃OD): δ 7.30 (d, 2H, J=8.1 Hz), 7.67 (d, 1H, J=5.1 Hz), 8.02 (d, 2H, J=8.1 Hz), 8.17 (s, 1H), 8.70 (d, 1H, J=5.1 Hz).

2-(4-Methoxyphenyl)pyridine-4-carboxamide (8g): ¹H NMR (400 MHz, CD₃OD): δ 3.82 (s, 3H), 6.98 (d, 2H, J=8.9 Hz), 7.59 (dd, 1H, J=1.6, 5.1 Hz), 7.89 (d, 2H, J=8.8 Hz), 8.11 (s, 1H), 8.63 (d, 1H, J=5.1 Hz).

2-(4-Ethoxyphenyl)pyridine-4-carboxamide (8h): ¹H NMR (400 MHz, CD₃OD): δ 1.46 (t, 3H, J=7.0 Hz), 4.13 (q, 2H, J=7.0 Hz), 7.03 (d, 2H, J=8.9 Hz), 7.63 (dd, 1H, J=1.6, 5.1 Hz), 7.94 (d, 2H, J=8.9 Hz), 8.16 (s, 1H), 8.70 (d, 1H, J=5.2 Hz).

Example 3

2-[4-(4-Fluorophenoxy)phenyl]pyridine-3-carboxamide (10)

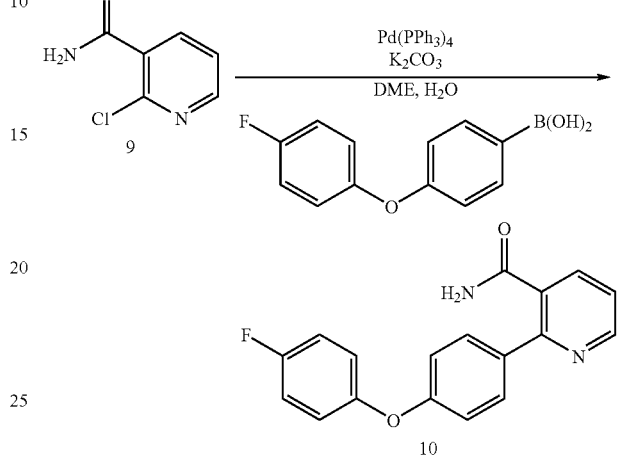

Compound 10 was prepared in a manner similar to the procedure described for compounds 8a-8h in Example 2 using compound 9 and 4-(4-fluorophenoxy)phenyl boronic acid. ¹H NMR (400 MHz, CD₃OD). δ 7.02-7.42 (m, 5H), 7.65 (d, 2H, J=8.8 Hz), 7.97-8.02 (m, 2H), 8.45 (d, 1H, J=4.9 Hz), 8.68 (d, 1H, J=4.9 Hz).

2-[4-(4-Fluorophenoxy)phenyl]pyridine-4-carboxamide was prepared similarly using compound 7 and 4-(4-fluorophenoxy)phenyl boronic acid. ¹H NMR (400 MHz, CDCl₃): δ 6.05 (bs, 1H), 6.31 (bs, 1H), 7.04-7.11 (m, 6H), 7.51 (d, 1H, J=5.0 Hz), 8.03 (d, 2H, J=8.8 Hz), 8.10 (s, 1H), 8.81 (d, 1H, J=5.0 Hz).

Example 4

5-(4-tert-Butylphenyl)pyridine-3-carboxamide (15a)

5-(4-Phenoxyphenyl)pyridine-3-carboxamide (15b)

5-(4-Ethoxyphenyl)pyridine-3-carboxamide (15c)

5-(4-Methoxyphenyl)pyridine-3-carboxamide (15d)

5-(4-n-Butylphenyl)pyridine-3-carboxamide (15e)

5-(2-Naphthyl)pyridine-3-carboxamide (15f)

5-(4-Thiomethylphenyl)pyridine-3-carboxamide (15g)

5-(4-Trifluoromethoxyphenyl)pyridine-3-carboxamide (15h)

5-(4-Trifluoromethylphenyl)pyridine-3-carboxamide (15i)

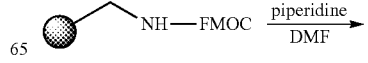

11

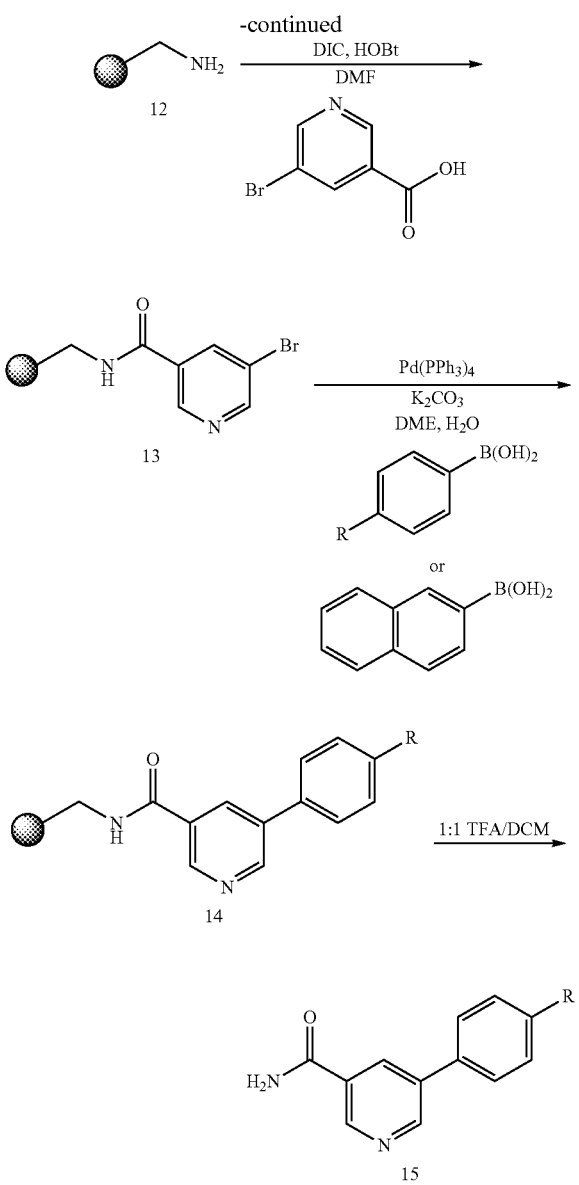

a R = tert-butyl
b R = OPh
c R = OEt
d R = OMe
e R = n-butyl
f naphthyl
g R = SMe
h R = OCF₃
i R = CF₃ a) Compound 13: 20% piperidine in DMF was added to polystyrene-Rink-amide resin having 9-fluorenylmethoxycarbonyl (FMOC) protective group (PS-rink-NH-FMOC resin) (11) (4.45 g, 4.14 mmol) in a solid-phase reaction vessel, and the reaction was shaken for 1.5 hours at ambient temperature. The resin was washed (DMF twice, dichloromethane twice, DMF) and then treated again with 20% piperidine in DMF. It was shaken for an additional hour, and the washing sequence was repeated. DMF was added to the resin, followed by N-hydroxybenzotriazole (HOBt) (3.4 g, 24.8 mmol), 5-bromonicotinic acid (5.0 g, 24.8 mmol), and a solution of 5-(3,4-dimethyl-1-triazenyl)-1H-imidazole-4-carboxamide (DIC) (3.1 g, 24.8 mmol) in DMF. The mixture was shaken for 24 hours at ambient temperature and then drained. The resin was washed (DMF twice, dichloromethane twice, DMF) and dried. Compound 13 was split into individual reaction vessels.

b) Compounds 14a-14i: 1,2-Dimethoxyethane (2.5 mL) was added to the individual reaction vessels containing compound 13 (0.25 mmol), followed by the addition of the appropriate phenyl boronic acid (1.5 mmol). To this mixture was added water (1.0 mL), potassium carbonate (3.8 mmol), and Pd(PPh₃)₄ (0.043 mmol). The reactions were heated at 85° C. for 16 hours. After returning to ambient temperature, the reactions were drained, and the resin was washed (1:1 DME-water twice, water, 1:1 DME-water twice, DME twice, water twice, THF twice, dichloromethane twice) to yield compounds 14a-14i.

c) Compounds 15a-15i: Compounds 14a-14i were shaken in the presence of 1:1 TFA-dichloromethane for 1.5 hours. The reactions were filtered, the resins were washed with dichloromethane, and the solvent was then evaporated. Purification of compounds 15a-15i was carried out by first filtering over a bed of florisil followed by subjection to silica gel chromatography.

5-(4-tert-Butylphenyl)pyridine-3-carboxamide (15a): $^1$H NMR (400 MHz, CD$_3$OD): δ 1.38 (s, 9H), 7.55 (d, 2H, J=8.6 Hz), 7.61 (d, 2H, J=8.5 Hz), 8.50 (s, 1H), 8.91 (bs, 1H), 8.89 (bs, 1H).

5-(4-Phenoxyphenyl)pyridine-3-carboxamide (15b): $^1$H NMR (400 MHz, CD$_3$OD): δ 7.06-7.42 (m, 7H), 7.67 (d, 2H, J=8.7 Hz), 8.49 (t, 1H, J=2.0 Hz), 8.91 (bs, 1H), 8.98 (bs, 1H).

5-(4-Ethoxyphenyl)pyridine-3-carboxamide (15c): $^1$H NMR (400 MHz, CD$_3$OD): δ 1.46 (t, 3H, J=7.0 Hz), 4.11 (q, 2H, J=7.0 Hz), 7.04 (d, 2H, J=8.6 Hz), 7.62 (d, 2H, J=8.6 Hz), 8.56 (s, 1H), 8.92 (bs, 1H), 8.98 (bs, 1H).

5-(4-Methoxyphenyl)pyridine-3-carboxamide (15d): $^1$H NMR (400 MHz, CD$_3$OD): δ 4.38 (s, 3H), 7.03 (d, 2H, J=8.8 Hz), 7.60 (d, 2H, J=8.8 Hz), 8.80 (s, 1H), 8.95 (bs, 2H).

5-(4-n-Butylphenyl)pyridine-3-carboxamide (15e): $^1$H NMR (400 MHz, CD$_3$OD): δ 1.03 (t, 3H, J=7.3 Hz), 1.44-1.49 (m, 2H), 1.70-1.76 (m, 2H), 2.76 (t, 2H, J=7.6 Hz), 7.40 (d, 2H, J=8.8 Hz), 7.66 (d, 2H, J=8.8 Hz), 8.59 (t, 1H, J=2.0 Hz), 8.98 (bs, 1H), 9.04 (bs, 1H).

5-(2-Naphthyl)pyridine-3-carboxamide (15f): $^1$H NMR (400 MHz, CD$_3$OD): δ 7.56-8.04 (m, 6H), 8.19 (s, 1H), 8.73 (s, 1H), 9.06 (bs, 1H), 9.12 (bs, 1H).

5-(4-Thiomethylphenyl)pyridine-3-carboxamide (15g): $^1$H NMR (400 MHz, CD$_3$OD): δ 2.49 (s, 3H), 7.33 (d, 2H, J=8.5 Hz), 7.55 (d, 2H, J=8.5 Hz), 8.43 (s, 1H), 8.86 (bs, 1H), 8.92 (bs, 1H).

5-(4-Trifluoromethoxyphenyl)pyridine-3-carboxamide (15h): $^1$H NMR (400 MHz, CD$_3$OD): δ 7.34 (d, 2H, J=8.8 Hz), 7.69 (d, 2H, J=8.8 Hz), 8.46 (t, 1H, J=2.1 Hz), 8.87 (bs, 1H), 8.99 (bs, 1H).

5-(4-Trifluoromethylphenyl)pyridine-3-carboxamide (15i): $^{1}$H NMR (400 MHz, CD$_3$OD): δ 7.78-7.83 (m, 4H), 8.54 (t, 1H, J=2.1 Hz), 8.95 (bs, 1H), 9.07 (bs, 1H).

Example 5

2-(4-Trifluoromethoxyphenyl)pyridine-5-carboxamide (18a)

2-(4-Trifluoromethylphenyl)pyridine-5-carboxamide (18b)

2-(2-Naphthyl)pyridine-5-carboxamide (18c)

2-(4-Phenoxyphenyl)pyridine-5-carboxamide (18d)

2-(4-tert-Butylphenyl)pyridine-5-carboxamide (18e)

2-(4-Ethoxyphenyl)pyridine-5-carboxamide (18f)

2-(4-Thiomethylphenyl)pyridine-5-carboxamide (18g)

2-(4-Methoxyphenyl)pyridine-5-carboxamide (18h)

2-(4-n-Butylphenyl)pyridine-5-carboxamide (18i)

2-(4-Phenylphenyl)pyridine-5-carboxamide (18j)

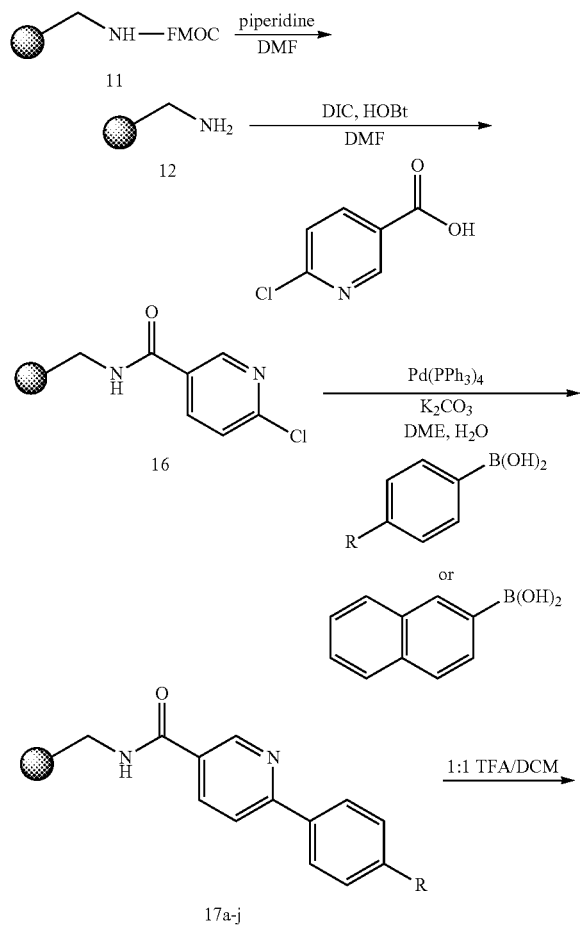

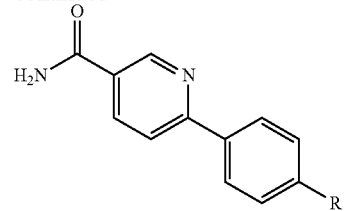

a R = OCF$_3$
b R = CF$_3$
c naphthyl
d R = OPh
e R = tert-butyl
f R = OEt
g R = SMe
h R = OMe
i R = n-butyl
j R = Ph a) Compound 16: Compound 16 was prepared in a manner similar to the procedure described for compound 13 in Example 4 using 6-chloronicotinic acid and compound 12.

b) Compounds 17a-17j: Compounds 17a-17j were prepared in a manner similar to the procedure described for compound 14 in Example 4 using compound 16 and the appropriate phenyl boronic acid.

c) Compounds 18a-18j: Compounds 18a-18j were prepared in a manner similar to the procedure described for compound 15 in Example 4.

2-(4-Trifluoromethoxyphenyl)pyridine-5-carboxamide (18a): $^{1}$H NMR (400 MHz, CD$_3$OD): δ 7.37 (d, 2H, J=8.0 Hz), 7.87 (d, 1H, J=8.3 Hz), 8.06 (d, 2H, J=8.9 Hz), 8.32 (dd, 1H, J=2.3, 8.3 Hz), 9.10-9.11 (m, 1H).

2-(4-Trifluoromethylphenyl)pyridine-5-carboxamide (18b): $^{1}$H NMR (400 MHz, CD$_3$OD): δ 7.78 (d, 2H, J=8.0 Hz), 7.91 (d, 1H, J=8.2 Hz), 8.14 (d, 2H, J=8.0 Hz), 8.35 (d, 1H, J=8.3 Hz), 9.14 (s, 1H).

2-(2-Naphthyl)pyridine-5-carboxamide (18c): $^{1}$H NMR (400 MHz, CD$_3$OD): δ 7.54-7.57 (m, 2H), 7.98-8.09 (m, 5H), 8.35 (dd, 1H, J=2.3, 8.3 Hz), 8.48 (bs, 1H), 9.13 (d, 1H, J=2.2 Hz).

2-(4-Phenoxyphenyl)pyridine-5-carboxamide (18d): $^{1}$H NMR (400 MHz, CD$_3$OD): δ 7.08-7.20 (m, 5H), 7.38-7.44 (m, 2H), 7.82 (d, 1H, J=8.3 Hz), 7.97 (d, 2H, J=8.9 Hz), 8.29 (dd, 1H, J=2.3, 8.3 Hz), 9.07 (m, 1H).

2-(4-tert-Butylphenyl)pyridine-5-carboxamide (18e): $^{1}$H NMR (400 MHz, CD$_3$OD): δ 1.32 (s, 9H), 7.52 (d, 2H, J=8.9 Hz), 7.81 (d, 1H, J=8.3 Hz), 7.89 (d, 2H, J=8.9 Hz), 8.25 (dd, 1H, J=2.3, 8.3 Hz), 9.04 (d, 1H, J=2.3 Hz).

2-(4-Ethoxyphenyl)pyridine-5-carboxamide (18f): $^{1}$H NMR (400 MHz, CD$_3$OD): δ 1.46 (t, 3H, J=7.0 Hz), 4.13 (q, 2H, J=7.0 Hz), 7.03 (d, 2H, J=8.9 Hz), 7.79 (d, 1H, J=8.4 Hz), 7.93 (d, 2H, J=8.9 Hz), 8.26 (dd, 1H, J=2.3, 8.4 Hz), 9.02 (d, 1H, J=2.2 Hz).

2-(4-Thiomethylphenyl)pyridine-5-carboxamide (18g): $^{1}$H NMR (400 MHz, CD$_3$OD): δ 2.55 (s, 3H), 7.39 (d, 2H, J=8.9 Hz), 7.87 (d, 1H, J=8.3 Hz), 7.93 (d, 2H, J=8.9 Hz), 8.31 (dd, 1H, J=2.3, 8.3 Hz), 9.09 (d, 1H, J=2.3 Hz).

2-(4-Methoxyphenyl)pyridine-5-carboxamide (18h): $^{1}$H NMR (400 MHz, CD$_3$OD): δ 3.90 (s, 3H), 7.05 (d, 2H, J=8.9 Hz), 7.81 (d, 1H, J=8.3 Hz), 7.95 (d, 2H, J=8.9 Hz), 8.27 (dd, 1H, J=2.3, 8.3 Hz), 9.05 (d, 1H, J=2.3 Hz).

2-(4-n-Butylphenyl)pyridine-5-carboxamide (18i): $^{1}$H NMR (400 MHz, CD$_3$OD): δ 0.95 (t, 3H, J=7.3 Hz), 1.36-1.42 (m, 2H), 1.61-1.70 (m, 2H), 2.69 (t, 2H, J=7.7 Hz), 7.33

(d, 2H, J=8.3 Hz), 7.83 (d, 1H, J=8.3 Hz), 7.89 (d, 2H, J=8.3 Hz), 8.29 (dd, 1H, J=2.3, 8.3 Hz), 9.06 (d, 1H, J=2.3 Hz).

2-(4-Phenylphenyl)pyridine-5-carboxamide (18j): $^1$H NMR (400 MHz, CD$_3$OD): δ 7.37-7.69 (m, 5H), 7.70 (d, 2H, J=8.4 Hz), 7.95 (d, 1H, J=8.3 Hz), 8.09 (d, 2H, J=8.4 Hz), 8.34 (dd, 1H, J=2.3, 8.3 Hz), 9.13 (d, 1H, J=2.1 Hz).

Example 6

Activity of 2-[4-(4-fluorophenoxy)phenyl]pyridine 5-carboxylic acid 2-(N-piperidinyl)ethylamide as Sodium Channel Blocker 2-[4-(4-Fluorophenoxy)phenyl]pyridine 5-carboxylic acid 2-(N-piperidinyl)ethylamide was tested in the electrophysiological assay as described above. The result of 2-[4-(4-fluorophenoxy)phenyl]pyridine 5-carboxylic acid 2-(N-piperidinyl)ethylamide and other compounds are represented in Table 1.

TABLE 1

Evaluation of the Tested Compounds as Sodium Channel Blockers after an Electrophysiological in vitro Assay

| Compound name | RBIIA/β1 $K_i$/μM |
|---|---|
| 2-[4-(4-fluorophenoxy)phenyl]pyridine 5-carboxylic acid 2-(N-piperidinyl)ethylamide | 0.95 |
| 5-[4-(4-fluorophenoxy)phenyl]pyridine 3-carboxylic acid 2-(N-piperidinyl)ethylamide | 0.78 |
| 2-[4-(4-fluorophenoxy)phenyl]pyridine-3-carboxamide | 13.57 |
| 2-[4-(4-fluorophenoxy)phenyl]pyridine-4-carboxamide | 6.91 |
| 2-(4-phenoxyphenyl)pyridine-5-carboxamide | 14.62 |
| 2-(4-phenoxyphenyl)pyridine-4-carboxamide | 22.28 |
| 5-(4-phenoxyphenyl)pyridine-3-carboxamide | 5.43 |
| 5-(2-naphthyl)pyridine-3-carboxamide | 35.12 |
| 2-(2-naphthyl)pyridine-5-carboxamide | 28.06 |
| 2-(2-phenylphenyl)pyridine-4-carboxamide | 24.85 |
| 2-(2-phenylphenyl)pyridine-5-carboxamide | 40.68 |
| 5-(4-tert-butylphenyl)pyridine-3-carboxamide | 18.55 |
| 2-(4-tert-butylphenyl)pyridine-4-carboxamide | 53.12 |
| 2-(4-tert-butylphenyl)pyridine-5-carboxamide | 32.32 |
| 2-(4-i-propylphenyl)pyridine-4-carboxamide | 39.17 |
| 5-(4-thiomethylphenyl)pyridine-3-carboxamide | 28.97 |
| 2-(4-thiomethylphenyl)pyridine-5-carboxamide | 35.65 |
| 5-(4-trifluoromethoxyphenyl)pyridine-3-carboxamide | 24.98 |
| 2-(4-trifluoromethoxyphenyl)pyridine-5-carboxamide | 34.16 |
| 2-(4-trifluoromethoxyphenyl)pyridine-4-carboxamide | 24.67 |
| 5-(4-trifluoromethylphenyl)pyridine-3-carboxamide | 23.03 |
| 2-(4-trifluoromethylphenyl)pyridine-5-carboxamide | 24.67 |
| 2-(4-n-butylphenyl)pyridine-4-carboxamide | 32.92 |
| 2-(4-methoxyphenyl)pyridine-4-carboxamide | 6.17 |
| 2-(4-ethoxyphenyl)pyridine-4-carboxamide | 14.72 |
| 5-(4-ethoxyphenyl)pyridine-3-carboxamide | 36.22 |
| 5-(4-methoxyphenyl)pyridine-3-carboxamide | 54.41 |
| 5-(4-n-butylphenyl)pyridine-3-carboxamide | 11.05 |
| 2-(4-ethoxyphenyl)pyridine-5-carboxamide | 29.69 |
| 2-(4-methoxyphenyl)pyridine-5-carboxamide | 44.56 |
| 2-(4-n-butylphenyl)pyridine-5-carboxamide | 24.54 |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound having the Formula I:

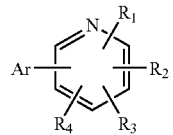

or a pharmaceutically acceptable salt thereof, wherein:
Ar is Ar$_3$, wherein
Ar$_3$ is

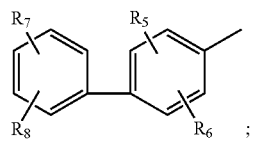

R$_1$ is C(O)R$_{10}$;
R$_2$, R$_3$, and R$_4$ are independently selected from the group consisting of hydrogen, optionally substituted alkyl, alkenyl, or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino;
provided that
the pyridyl ring is other than 2,6-disubstituted with regard to Ar and R$_1$ or any of R$_2$-R$_4$ that is other than hydrogen;
R$_5$, R$_6$, R$_7$, and R$_8$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, carbonylamido and alkylthiol; and
R$_{10}$ is selected from the group consisting of alkyl, alkenyl, alkynyl, OR$_{11}$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which are optionally substituted, wherein
R$_{11}$ is selected from the group consisting of hydrogen, optionally substituted alkyl, and an alkali metal.

2. The compound of claim 1, wherein R$_{10}$ is selected from the group consisting of alkyl, alkenyl, OR$_{11}$, amino, alkylamino, dialkylamino, alkenylamino, dialkylaminoalkenyl, dialkylaminoalkylamino, and heterocycloalkylamino, all of which are optionally substituted.

3. The compound of claim 1, wherein R$_2$, R$_3$ and R$_4$ are independently selected from the group consisting of hydrogen, alkyl, alkenyl, alkynyl, aminoalkyl, amino, hydroxyalkyl, alkoxy, aminocarbonyl, alkylaminocarbonyl, arylaminocarbonyl, aralkylaminocarbonyl, alkylcarbonylamino, arylcarbonylamino, and aralkylcarbonylamino.

4. The compound of claim 3, wherein R$_2$ is selected from the group consisting of hydrogen, alkyl, alkoxy, aminoalkyl and aminocarbonyl, and both R$_3$ and R$_4$ are hydrogen.

5. The compound of claim 1, wherein $R_5$, $R_6$, $R_7$, and $R_8$ are independently selected from the group consisting of hydrogen, alkyl, alkenyl, alkynyl, halogen, haloalkyl, hydroxyalkyl, hydroxy, nitro, amino, and cyano.

6. The compound of claim 5, wherein $R_5$ and $R_6$ are both hydrogen and $R_7$ and $R_8$ are independently selected from the group consisting of hydrogen, alkyl, halogen, haloalkyl, and nitro.

7. The compound of claim 1, having the Formula V:

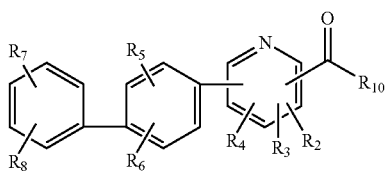

or a pharmaceutically acceptable salt, prodrug or solvate thereof, wherein:
$R_2$-$R_8$ are defined in claim 1; and
$R_{10}$ is amino or 2-(N-piperidinyl)ethylamino;
provided that the pyridyl ring is other than 2,6-disubstituted with regard to the biphenyl radical and —C(O)$R_{10}$ or any of $R_2$-$R_4$ that is other than hydrogen.

8. The compound of claim 7, wherein said compound is:
2-(4-phenylphenyl)pyridine-4-carboxamide;
2-(4-phenylphenyl)pyridine-5-carboxamide;
or a pharmaceutically acceptable salt thereof.

9. A pharmaceutical composition, comprising the compound of formula:

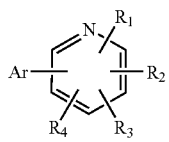

or a pharmaceutically acceptable salt thereof, wherein:
Ar is $Ar_3$, wherein
$Ar_3$ is

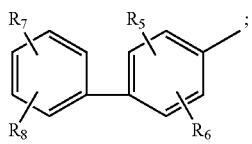

$R_1$ is C(O)$R_{10}$;
$R_2$, $R_3$, and $R_4$ are independently selected from the group consisting of hydrogen, optionally substituted alkyl, alkenyl, or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino;
provided that
the pyridyl ring is other than 2,6-disubstituted with regard to Ar and $R_1$ or any of $R_2$-$R_4$ that is other than hydrogen;
$R_5$, $R_6$, $R_7$, and $R_8$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, carbonylamido and alkylthiol; and
$R_{10}$ is selected from the group consisting of alkyl, alkenyl, alkynyl, OR$_{11}$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which are optionally substituted, wherein
$R_{11}$ is selected from the group consisting of hydrogen, optionally substituted alkyl, and an alkali metal; and
a pharmaceutically acceptable carrier or diluent.

10. A method for treating or ameliorating pain, comprising administering to a mammal in need of such treatment or amelioration an effective amount of a compound formula:

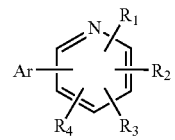

or a pharmaceutically acceptable salt thereof, wherein:
Ar is $Ar_3$, wherein
$Ar_3$ is

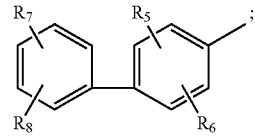

$R_1$ is C(O)$R_{10}$;
$R_2$, $R_3$, and $R_4$ are independently selected from the group consisting of hydrogen, optionally substituted alkyl, alkenyl, or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino;
provided that
the pyridyl ring is other than 2,6-disubstituted with regard to Ar and $R_1$ or any of $R_2$-$R_4$ that is other than hydrogen;
$R_5$, $R_6$, $R_7$, and $R_8$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, carbonylamido and alkylthiol; and
$R_{10}$ is selected from the group consisting of alkyl, alkenyl, alkynyl, OR$_{11}$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which can be are optionally substituted, wherein $R_{11}$ is selected from the group consisting of hydrogen, optionally substituted alkyl, and an alkali metal.

11. The method of claim 10, wherein said pain is one of neuropathic pain, surgical pain or chronic pain.

12. A compound having the Formula I:

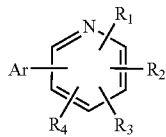

or a pharmaceutically acceptable salt thereof, wherein:
Ar is $Ar_3$, wherein
$Ar_3$ is

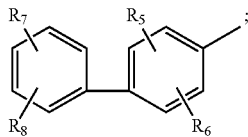

$R_1$ is $C(O)R_{10}$;

$R_2$, $R_3$, and $R_4$ are independently selected from the group consisting of hydrogen, optionally substituted alkyl, alkenyl, or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino;

provided that the pyridyl ring is other than 2,6-disubstituted with regard to Ar and $R_1$ or any of $R_2$-$R_4$ that is other than hydrogen;

$R_5$, $R_6$, $R_7$, and $R_8$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, carbonylamido and alkylthiol; and $R_{10}$ is selected from the group consisting of alkyl, alkenyl, alkynyl, $OR_{11}$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which are optionally substituted, wherein $R_{11}$ is selected from the group consisting of hydrogen, optionally substituted alkyl, and an alkali metal;

wherein said compound is $^3H$ or $^{14}C$ radiolabeled.

13. A method of screening for a candidate compound for treating or ameliorating pain that binds to a receptor using a radiolabeled compound of claim 12, comprising:

introducing a fixed concentration of the radiolabeled compound to the receptor to form a mixture;
titrating the mixture with a candidate compound; and
determining the binding of the candidate compound.

* * * * *